US010143739B2

(12) United States Patent
Chang et al.

(10) Patent No.: US 10,143,739 B2
(45) Date of Patent: Dec. 4, 2018

(54) VACCINES FOR PORCINE EPIDEMIC DIARRHEA VIRUS INFECTIONS

(71) Applicant: Kansas State University Research Foundation, Manhattan, KS (US)

(72) Inventors: Kyeong-Ok Chang, Manhattan, KS (US); Yunjeong Kim, Manhattan, KS (US); Richard A. Hesse, Valley, NE (US)

(73) Assignee: KANSAS STATE UNIVERSITY RESEARCH FOUNDATION, Manhattan, KS (US)

( * ) Notice: Subject to any disclaimer, the term of this patent is extended or adjusted under 35 U.S.C. 154(b) by 0 days.

(21) Appl. No.: 15/548,074

(22) PCT Filed: Feb. 3, 2016

(86) PCT No.: PCT/US2016/016417
§ 371 (c)(1),
(2) Date: Aug. 1, 2017

(87) PCT Pub. No.: WO2016/126853
PCT Pub. Date: Aug. 11, 2016

(65) Prior Publication Data
US 2018/0008699 A1    Jan. 11, 2018

Related U.S. Application Data

(60) Provisional application No. 62/111,324, filed on Feb. 3, 2015.

(51) Int. Cl.
*A61K 39/225* (2006.01)
*A61K 39/00* (2006.01)
*A61K 39/12* (2006.01)

(52) U.S. Cl.
CPC ............ *A61K 39/225* (2013.01); *A61K 39/12* (2013.01); *A61K 2039/5254* (2013.01); *A61K 2039/552* (2013.01); *C12N 2770/18034* (2013.01)

(58) Field of Classification Search
None
See application file for complete search history.

(56) References Cited

U.S. PATENT DOCUMENTS

2018/0008699 A1*    1/2018    Chang ................. A61K 39/225

FOREIGN PATENT DOCUMENTS

CN        103725651        4/2014

OTHER PUBLICATIONS

Wicht et al. (Journal of Virology. Jul. 2014; 88 (14): 7952-7961).*
Geisler et al. (Journal of Immunology. 2005; 174: 6431-6439).*
Shivanna et al. (Virology. 2014; 456-457: 268-278).*
The International Search Report and Written Opinion dated May 9, 2016, in PCT/US2016/016417 filed on Feb. 3, 2016.

(Continued)

*Primary Examiner* — Shanon A. Foley
(74) *Attorney, Agent, or Firm* — Hovey Williams LLP

(57) ABSTRACT

Isolated porcine epidemic diarrhea virus (PEDV) deposited under ATCC Accession No. PTA-121847, and attenuated strains generated by serial passage in culture of the deposited strain. Immunogenic compositions for reducing the incidence or severity of clinical symptoms from PEDV infection, and methods of making and using the same.

20 Claims, 7 Drawing Sheets

Specification includes a Sequence Listing.

(56) References Cited

OTHER PUBLICATIONS

Park, Jung-Eun, "Clathrin- and serine proteas es-dependent uptake of porcine epidemic diarrhea virus into Vero cells," Virus Research, Jul. 31, 2014, pp. 21-29, vol. 191.

Cromeans, Theresa, "Comprehensive Comparison of Cultivable Norovirus Surrogates in Response to Different Inactivation and Disinfection Treatments," Applied and Environmental Microbiology, Jul. 11, 2014.

\* cited by examiner

No virus

PEDV 8aa in simple MEM

PEDV 8aa with GCDCA

PEDV 8aa in trypsin, 1 ug/ml

B

← N protein 1 2 3 4 5

1. Mock
2. GCDCA 100 uM
3. Trypsin 1 ug/ml
4. Trypsin 0.1 ug/ml
5. Trypsin 0.01 ug/ml

FIG. 3

VACCINES FOR PORCINE EPIDEMIC DIARRHEA VIRUS INFECTIONS

CROSS-REFERENCE TO RELATED APPLICATIONS

The present application is the National Stage of International Patent Application No. PCT/US2016/016417, filed Feb. 3, 2016, which claims the priority benefit of U.S. Provisional Patent Application Ser. No. 62/111,324, filed Feb. 3, 2015 entitled. Novel Vaccines for Porcine Epidemic Diarrhea Virus Infections, each of which is incorporated by reference in its entirety herein.

SEQUENCE LISTING

The following application contains a sequence listing in computer readable format (CRF), submitted as a text file in ASCII format entitled "46731-PCTSequenceListing," created on Feb. 2, 2016, as 37 KB. The content of the CRF is hereby incorporated by reference.

BACKGROUND OF THE INVENTION

Field of the Invention

The present invention relates to attenuated strains of PEDV, vaccines and methods related to the same.

Description of Related Art

Porcine Epidemic Diarrhea Virus (PEDV) is a coronavirus that causes extreme dehydration and death of up to 100 percent of the affected neonatal piglets or severe diarrhea and vomiting in older pigs. The first PEDV case was reported in the UK 1971, and during the 1970s and 1980s, PEDV has spread throughout the Europe. The classical PEDV strain CV777 (phylogenetically classified as subgroup 1) was isolated in Belgium in 1976. In the last 30 years or so, subgroup 1 strains also caused outbreaks with extensive economic losses in some Asian countries with up to 80% to 100% morbidity and 50% to 90% mortality in suckling piglets. In the U.S., the first PEDV outbreaks occurred in 2013 and since then the US PEDV strains (subgroup 2a) PED has quickly spread to most states as well as Canada and Mexico. The U.S. PEDV strains were also reported to have caused outbreaks in Asia and European countries, raising significant economic and public health concerns worldwide. Modified live attenuated vaccines (MLVs) for PEDV subgroup 1 strains are available in the EU and Asian countries, and they have been the major means to control PEDV. However, the subgroup 1 MLVs may not provide effective protective immunity to the circulating subgroup 2a PEDV strains due to the genetic diversity (up to 10%). Currently only two conditionally approved vaccines exist in the US: alphavirus-based vaccine (Harris vaccines) and an inactivated vaccine (Zoetis). However, MLVs are not yet available for PEDV U.S. strains.

Administration of a MLV, followed by a booster dose of an inactivated vaccine or a MLV in pregnant sows is generally considered as an effective measure for controlling PEDV; MLV would effectively prime the immune system of the pregnant sows, especially the PEDV naïve sows, for the production of antibodies, which are transferred to neonatal piglets and protects them from viral infections during the most susceptible period (<2 weeks of age). There remains a significant need for live, attenuated vaccines against PEDV U.S. strains.

SUMMARY OF THE INVENTION

The present invention is broadly concerned with live, attenuated porcine epidemic diarrhea virus (PEDV) strains generated by serial passage in culture of an isolated PEDV strain deposited under ATCC Accession No. PTA-121847.

Immunogenic compositions are also disclosed, which comprise the PEDV strains attenuated according to the invention, dispersed in a pharmaceutically-acceptable carrier.

Also described are methods of reducing the incidence or severity of clinical symptoms of PEDV infection in a subject. The methods generally comprise administering to the subject an immunogenic composition according to various embodiments of the invention.

A kit for inducing an immune response against PEDV infection in a subject is also disclosed. The kit comprises an immunogenic composition comprising the live, attenuated PEDV strain(s) of the invention; and instructions for administering the immunogenic composition to the subject.

Also disclosed is the use of an immunogenic composition comprising the live, attenuated PEDV according to the various embodiments of the invention for inducing an immune response against PEDV infection in a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure (FIG. 1) shows an image of Vero cells inoculated with serial dilution of each 8aa PEDV passage and incubated with 1 µg/ml trypsin, then fixed with 4% formaldehyde and stained with crystal violet;

FIG. 2 shows growth of PEDV 8aa (P21) in various culture conditions determined using: A. IFA; and B. Western blot analysis;

FIG. 3 shows an image of Western Blot analysis of serial dilutions of concentrated PEDV KD (P120), PEDV AA (P103) or PEDV 8aa (P70) with anti-PEDV antisera;

DETAILED DESCRIPTION

Figure 1:
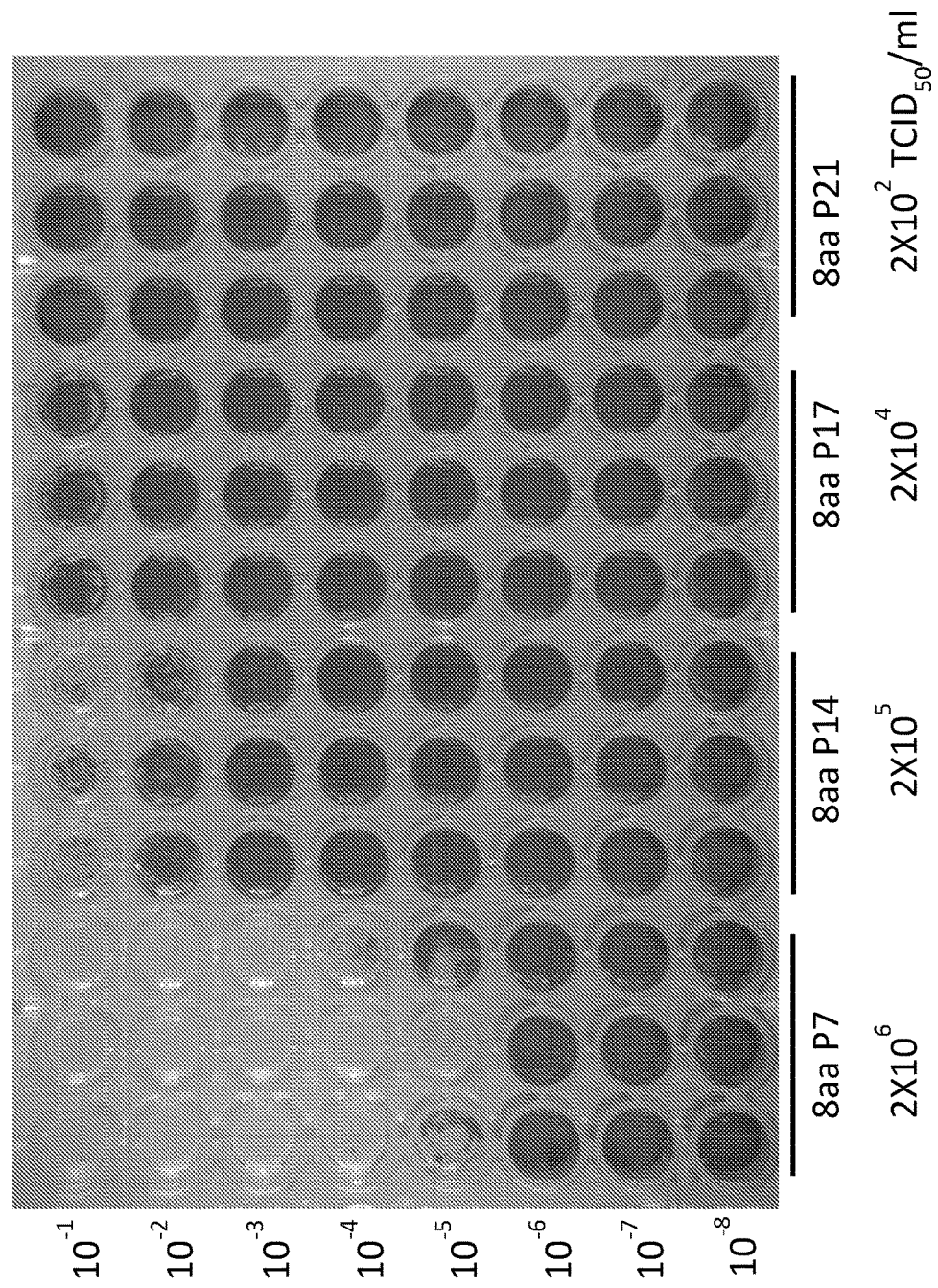

The invention is directed towards PEDV strains from the United States, which are different from previously reported PEDV strains. The present invention is concerned with an attenuated PEDV RNA virus generated from an isolated U.S. PEDV strain, immunogenic compositions for vaccination against PEDV infection, and methods related to the same. In particular, the invention is concerned with a PEDV strain, designated as 8aa PEDV P40 deposited with the American Type Culture Collection, located at 10801 University Boulevard, Manassas, Va. 20110-2209, on Dec. 11, 2014, under the provisions of the Budapest Treaty, with ATCC Accession No. PTA-121847, which is hereby incorporated by reference. The PEDV strain deposited with the ATCC was attenuated by serial passage in Vero cells in culture containing glycochenodeoxycholic acid (GCDCA) at least 40 times (P40). In one or more embodiments, the invention is concerned with live, attenuated virus derived from further serial passage of 8aa PEDV P40 (i.e., progeny of the deposited virus). The terms "derived" or "generated" from refer to creation of progeny (aka derivatives) of the deposited strain through subsequent passaging in cell culture under conditions described herein (e.g., in conjugated bile acids, simple media, enzyme-free media, etc.). In one or more embodiments, the invention is concerned with PEDV deposited under ATCC Accession No. PTA-121847, which has subsequently been serially passaged in culture at least 30 additional times, to generate fully attenuated progeny virus designated herein as PEDV 8aa P70. In one or more embodiments, the strain has been serially passaged in culture at least 65 additional times, to generate fully attenuated progeny virus designated herein as PEDV 8aa P105. Thus, in preferred embodiments, the invention is concerned with PEDV ATCC Accession No. PTA-121847 passaged at least 70 times total (P70), and preferably at least 105 times total (P105), preferably in culture containing bile acids (such as GCDCA). In some embodiments, the PEDV can be propagated without addition of any enzyme or GCDCA in the media after passage number 20. More preferably, the virus is passaged without trypsin and/or elastase. In one or more embodiments, the culture for serial passaging of the virus is substantially free of elastase, trypsin, and/or GCDCA. The term "substantially free," as used herein, means that the ingredient is not purposefully added to the composition, it being understood that trace amounts or impurities may still be present in the composition without departing from the invention. In other words, the excluded ingredient is preferably present in amounts of less than about 0.1 μg/ml, preferably less than about 0.1 ug/ml. Preferably, the culture medium for passaging the virus comprises simple minimum essential medium (MEM) with or without GCDCA (100 μM) or fetal bovine serum (FBS).

Thus, in preferred embodiments, the PEDV is enzyme-independent, and specifically trypsin- or elastase-independent. The term "enzyme-independent" and related terms means that the virus does not require the enzyme for growth, and can be grown in culture without enzymes. This enzyme-independent PEDV consistently yields higher titers ($>1\times10^8$ $TCID_{50}$/ml) with or without GCDCA (100 μM) than PEDV grown in elastase (about $5\times10^6$ $TCID_{50}$/ml) or trypsin (about $5\times10^6$ $TCID_{50}$/ml). In one embodiment of the invention, methods of generating enzyme-independent virus using bile acids are disclosed. Methods of attenuating PEDV by passaging enzyme-independent PEDV in the presence of bile acids at least 20 passages, followed by passaging in culture with or without bile acids at least 50 times (for a total of P70) are also described. High-passaged (>P100) enzyme-dependent PEDV is also disclosed. After over 10-20 passages, growth of this enzyme-independent-PEDV (PEDV 8aa) is severely limited in the presence of trypsin or elastase in cell culture; thus it exhibits attenuation in swine. In one or more embodiments, the enzyme-independent PEDV has restricted growth in culture in the presence of trypsin and/or elastase ($<1\times10^2$ $TCID_{50}$/ml). The enzyme-independent PEDV is fully attenuated in vivo at P70 or later. More specifically, as demonstrated in the examples, high-passaged (P70 or P105) enzyme-independent PEDV is fully attenuated in 1 or 2-day old piglets when inoculated through oral gavage.

One embodiment of the invention comprises an attenuated vaccine (immunogenic composition) for use in swine to reduce the incidence of or lessen the severity of PEDV infection in swine, and methods of reducing the incidence of or reducing the severity of clinical symptoms associated with PEDV in swine. Clinical symptoms associated with PEDV infection include loose stool, viral shedding, diarrhea, weight loss, anorexia (food aversion), lethargy, and/or mortality. In some aspects, the compositions lessen the amount or length of viral shedding or the length of time that such symptoms are presented. In some aspects, the compositions lessen the amount or length of time of diarrhea, or the length of time that such symptoms are presented.

The compositions comprise an attenuated PEDV RNA virus, described herein, dispersed in a pharmaceutically-acceptable carrier. The composition can comprise a therapeutically effective amount of the virus dispersed in the carrier. As used herein, a "therapeutically effective" amount refers to the amount that will elicit the biological or medical response of a tissue, system, or subject that is being sought by a researcher or clinician, and in particular elicit some desired therapeutic or prophylactic effect as against the viral infection by inhibiting viral replication and/or lessening the severity of the infection. One of skill in the art recognizes that an amount may be considered therapeutically "effective" even if the condition is not totally eradicated or prevented, but it or its symptoms and/or effects are improved or alleviated partially in the subject. In one or more embodiments, the compositions will comprise at least about $1\times10^7$ $TCID_{50}$ (tissue culture infectious dose affecting 50% of cultures inoculated) attenuated PEDV per unit dose, and preferably from about $1\times10^4$ to about $1\times10^9$ $TCID_{50}$ attenuated PEDV per unit dose. In other words, concentration of virus in each dose should be up to about 7 $\log_{10}$ $TCID_{50}$/ml, more preferably from about 4 to about 9 $\log_{10}$ $TCID_{50}$/ml, and still more preferably from about 6 to about 8 $\log_{10}$ $TCID_{50}$/ml. The therapeutically effective dosage of attenuated virus may vary depending on the size and species of the subject, and according to the mode of administration.

The term carrier is used herein to refer to diluents, excipients, vehicles, and the like, in which the attenuated virus may be dispersed for administration. Suitable carriers will be pharmaceutically acceptable. Suitable carriers include those acceptable for veterinary use as well as human pharmaceutical use, and will depend on the route of administration. Exemplary carriers include aqueous solutions such as water, normal (n.) saline (~0.9% NaCl), phosphate buffered saline (PBS), sterile water/distilled autoclaved water (DAW), dextrose, various oil-in-water or water-in-oil emulsions, as well as dimethyl sulfoxide (DMSO), ethanol, glycerol, or other acceptable diluents, and the like. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would naturally be selected to minimize any degradation of the virus or other agents and to minimize any adverse side effects in the subject, as would be well known to one of skill in the art.

Additional pharmaceutically-acceptable ingredients for use in the compositions include adjuvants, additional antigens, buffering agents, salts, stabilizing agents, diluents, preservatives, antibiotics, isotonic agents, cell media (e.g., MEM, FBS), flavoring agents, and the like. Exemplary isotonic agents include dextrose, lactose, sugar alcohols (e.g., sorbitol, mannitol), and the like. Stabilizing agents include sugars such as sucrose and lactose, amino acids such as glycine or the monosodium salt of glutamic acid and proteins such as albumin or gelatin, and mixtures thereof. Exemplary preservatives include formaldehyde, thimerosal, and the like. The term "adjuvant" refers to components that potentiate or modulate the immune response to the active agent (in this case, the attenuated virus). Exemplary adjuvants include aluminum salts, (e.g., $Al(OH)_3$, $AlPO_4$, etc.), mineral oils, plant oils, squalene (AS03, MF59), saponins (QS-21), and the like. When present, adjuvant can be used in the composition at a concentration of about 0.01 to about 50%, preferably from about 2% to about 30%, more preferably from about 5% to about 25%, and most preferably from about 10% to about 20% by volume of the total immunogenic composition, taken as 100% by volume.

Compositions according to the embodiments disclosed herein are useful in treating viral infection from PEDV in a subject (e.g., swine) and/or preventing or reducing clinical symptoms of infection. Thus, embodiments described herein have therapeutic and/or prophylactic uses, and in particular can be used for prophylactic treatment of a viral infection. In general, the compositions are administered prophylactically, that is, before the subject demonstrates detectable clinical signs of an infection, such that the subject develops an adaptive immune response to infection by the virus. As such, the methods are useful for preventing the development of observable clinical symptoms from viral infection, and/or reducing the incidence or severity of clinical symptoms and/or effects of the infection, and/or reducing the duration of the infection/symptoms/effects, and/or reducing viral shedding (e.g., excretion or expulsion of the virus or viral particles from an infected subject), and/or reducing the duration of excretion of the virus or viral particles from an infected subject. Thus, the composition may only partially prevent and/or lessen the extent of morbidity due to the viral infection (i.e., reduce the severity of the symptoms and/or effects of the infection, and/or reduce the duration of the infection/symptoms/effects). Yet, the composition is still considered is still considered to treat or prevent the target infection or disease.

The methods comprise administering the immunogenic composition to a subject. In general, the subject would be an animal susceptible to PEDV. In some embodiments, the immunogenic composition is administered to a pregnant animal to induce immunity indirectly in her offspring through passive transfer of maternal antibodies. For example, the invention is particularly concerned with methods of conferring immunity to piglets against PEDV by administering to pregnant sows an effective amount of the attenuated PEDV, wherein the resulting piglet(s) have a reduced morbidity and/or mortality as compared to piglets born by unvaccinated sows. The disclosed embodiments are suitable for various routes of administration, depending upon the particular carrier and other ingredients used. For example, the compositions can be injected intramuscularly, subcutaneously, intradermally, or intravenously. They can also be administered via mucosa such as intranasally, but in preferred embodiments are administered orally. Oral administration may encompass, for example, adding the compositions to the feed or drink of the animals.

The aforementioned embodiments may be used in a combination therapy or as part of an immunization schedule in combination with other immunogenic agents and vaccines. In one embodiment of the invention, a prime-and-boost regimen can be employed, which is comprised of at least one primary administration and at least one booster administration of the attenuated virus.

Regardless, administration of the attenuated virus elicits an immune response in the animal (or offspring, if applicable). Such an "immune response" includes, for example, the production or activation of antibodies, B cells and/or the various T cells, directed specifically to an antigen or antigenic component of the attenuated virus. The immune response will be demonstrated by a lack of observable clinical symptoms, or reduction of clinical symptoms normally displayed by an infected animal, faster recovery times from infection, reduced duration or amount of viral shedding, and the like. Accordingly, vaccinated animals will display resistance to new infection (or observable signs of infection) or reduced severity of infection, as compared to unvaccinated animals. The invention is particularly concerned with pigs, in all stages of development, including newborn, embryonic, and fetal stages.

"Reducing" the incidence, severity, and/or duration of clinical symptoms and/or viral shedding, means reducing the number of infected animals in a group, reducing or eliminating the number of animals exhibiting clinical signs of infection, or reducing the severity of any clinical signs that are present in the animals, in comparison to wild-type infection in unvaccinated animals. Preferably, these are reduced in animals receiving the attenuated PEDV of the present invention by at least 10% in comparison to animals not receiving the vaccination which may become infected. More preferably, clinical symptoms of infection are reduced in animals receiving the vaccination by at least 20%, more preferably by at least 30%, even more preferably by at least 40%, and even more preferably by at least 50%.

In some embodiments, the vaccine can be provided in unit dosage form in a suitable container. The term "unit dosage form" refers to a physically discrete unit suitable as a unitary dosage for animal use. Each unit dosage form may contain a predetermined amount of the vaccine (and/or other active agents) in the carrier calculated to produce the desired effect. In other embodiments, the vaccine can be provided separate from the carrier (e.g., in its own vial, ampule, sachet, or other suitable container) for on-site mixing before administration to a subject. A kit comprising the immunogenic composition is also disclosed herein. The kit further comprises instructions for administering the vaccine to a subject. The virus can be provided as part of a dosage unit, already dispersed in a pharmaceutically-acceptable carrier, or it can be provided separately from the carrier. The kit can further comprise instructions for preparing the virus for administration to a subject, including for example, instructions for dispersing the virus in a suitable carrier.

The invention is also concerned with methods of attenuating PEDV and/or yielding high titer PEDV. The PEDV is "attenuated" which means a previously virulent virus that has been modified to substantially eliminate its virulent properties while retaining its immunogenicity. In one or more embodiments, an isolated (preferably wild type) PEDV strain is serially passaged in Vero cells under conditions suitable for production of infectious virus particles, and recovering the virus particles. The recovered virus is attenuated as compared to the original (wild type) isolated PEDV. More particularly, the method includes incubating the cells in culture containing elastase or conjugated bile acid to obtain elastase-adapted PEDV or enzyme-independent PEDV, respectively. In one embodiment of the invention the PEDV is grown and passaged in elastase at least 20 times. Elastase-passaged PEDV yields slightly higher titers ($5\times10^6$ $TCID_{50}$/ml) than PEDV grown in trypsin ($3\times10^6$ $TCID_{50}$/ml) when subsequently titrated with trypsin. In one or more embodiments, the PEDV is grown and passaged in conjugated bile acids (e.g., GCDCA) at least 20 times to yield enzyme-independent PEDV. Enzyme-independent PEDV at P20 can be subsequently propagated without bile acids in culture, but grows faster with them. Enzyme-independent PEDV can be cultured in simple MEM or FBS, with or without bile acids.

In addition to high titers of enzyme-independent PEDV, this has advantages over PEDV grown in trypsin (or elastase) in vaccine preparation: the proteolytic enzyme may affect cells or viruses during the course of viral culture and vaccine preparation, yielding inconsistent viral titers or altered antigens. In addition to the advantages of enzyme-independency of the viruses in vaccinology, one of the particularly useful applications of the enzyme-independent virus is the serum neutralizing assays: the serum in serum-neutralizing assays can interfere with the assay performance by inhibiting trypsin or elastase activity, yielding inconsistent results. Utilization of enzyme-independent viruses in such assays in diagnostics and/or evaluation of animal blood for PEDV antibodies provides more accurate and consistent results compared to the assays that use enzyme-dependent viruses.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Materials and Methods

Example 1—Isolation of US PEDV Strain and Materials

Vero cells were obtained from ATCC (Manassas, Va.), and maintained in Dulbecco's minimal essential medium (DMEM) containing 5% fetal bovine serum and antibiotics (chlortetracycline [25 µg/ml], penicillin [250 U/ml], and streptomycin [250 µg/ml]). The individual or pooled convalescent pig serum collected at 43 days after the virus inoculation from the pig challenge study were used as the source of anti-PEDV antibody. The pooled sera before the virus inoculation were used as the negative control. L-1-Tosylamide-2-phenylethyl chloromethyl ketone (TPCK)-treated trypsin and GCDCA were purchased from Sigma-Aldrich (St Louis, Mo.) and elastase from porcine pancreas was obtained from Promega (Madison, Wis.).

For the isolation of PEDV US strain, the day 4 intestinal contents from pig inoculated with a diagnostic sample (submitted from an Indiana farm who experienced with a PEDV outbreak in 2013) were diluted in minimum essential medium (MEM) for 1:10 and filtrated through a 0.2 um membrane filter. The prepared sample was inoculated to confluent Vero cells grown in 6-well plates and incubated in the presence of trypsin (1-2 µg/ml) in MEM without any supplement. After 4 days of the inoculation, virus infected cells (plates) were disrupted by 3 repeated freezing/thawing, and then the liquid was inoculated (passaged) into new Vero cells. After 2 passages, virus-specific cytopathic effects were observed, and it was further passaged in Vero cells. Viruses were further cloned with the limited dilution method for further passages.

Once the cloned virus was confirmed as PEDV by immunofluorescent assay (IFA) and the sequencing of spike (S) gene, it was further passaged under different conditions including the presence of trypsin (1 µg/ml), elastase (1 µg/ml) or glycochenodeoxycholic acid (GCDCA) (100 µM) in the media, and the resulting viruses were designated as PEDV KD, PEDV AA or PEDV 8aa, respectively, as described in more detail below. Viruses were further passaged in each condition for up to 120 passages. Every 3-5 passages, the titers of PEDV KD, PEDV AA or PEDV 8aa were determined by the $TCID_{50}$ method (Reed-Muench method) in the presence of trypsin (1 µg/ml), elastase (1 µg/ml) or GCDCA (100 µM), respectively.

In addition to these newly passaged viruses, we also introduced elastase (1 µg/ml) in the media of the cells infected with PEDV 8aa at passage number 120, and passaged 10 times in the presence of elastase. These cells were designated as PEDV 8aa E10. PEDV 8aa E10 was further passaged in the presence of trypsin (1 µg/ml) for 5 additional times, and the resulting virus was designated as PEDV 8aa T5. Various experiments, including real time qRT-PCR, IFA and Western blot analysis, were conducted for the characterization of PEDV KD, AA, 8aa, 8aa E10 and 8aa T5.

Example 2—Trypsin-Passaged PEDV (Designated as KD P1, P2, P3, Etc.)

PEDV was isolated and passaged in the presence of trypsin (1-2 µg/ml) as described in Example 1. After about 20 passages, virus began to grow faster (faster cytopathic effects (CPE) progress) and larger syncytia were seen in cell monolayers. At each passage, viruses were transferred to fresh Vero cells at a 1:1,000 dilution and harvested in less than 30 h following virus inoculation. The trypsin-adapted virus (designated herein as "KD") was deposited with the American Type Culture Collection, located at 10801 University Boulevard, Manassas, Va. 20110-2209, on Dec. 11, 2014, under the provisions of the Budapest Treaty, with ATCC Accession No. PTA-121846, which is hereby incorporated by reference.

Example 3—Elastase Passaged PEDV (Designated as AA P1, P2, P3, Etc.)

PEDV was originally isolated in the presence of trypsin as described in Example 1 and then passaged in the presence of pancreatic elastase (1-2 µg/ml). After about 10 passages, viruses began to grow faster (faster CPE progress). At each passage, fresh Vero cells were inoculated with virus at a 1:500 dilution and viruses were harvested in less than 30 h following virus inoculation. Elastase-passaged virus is also able to grow well in the presence of trypsin, and most viral titration was done with trypsin (1-2 µg/ml). Viruses were passaged in 6-well plates or 175 cm$^2$ flasks. The elastase-adapted virus (designated herein as "AA") was deposited with the American Type Culture Collection, located at 10801 University Boulevard, Manassas, Va. 20110-2209, on Dec. 11, 2014, under the provisions of the Budapest Treaty, with ATCC Accession No. PTA-121845, which is hereby incorporated by reference.

Example 4—PEDV Growing without any Enzyme (8Aa P1, P2, P3, Etc.)

PEDV was adapted to grow and passaged without any protease. This was achieved by passaging PEDV in Vero cells in the presence of conjugated bile acids (including GCDCA, 100 uM). The isolated PEDV described in Example 1 was inoculated in Vero cells and incubated with MEM containing various concentrations of GCDCA (1-200 µM) for 4 days. After that, virus infected cells (plates) were disrupted by 3 repeated freezing/thawing, and then the liquid was inoculated (passaged) into new Vero cells in the presence of GCDCA (100 After 3-4 passages, viruses grew well in the condition (simple MEM) without any enzyme in cell culture. Virus was further passaged with GCDCA (100 µM) by transferring to fresh Vero cells at a 1:200 dilution and harvested in less than 48 h following virus inoculation. This virus grows without forming syncytium which is a characteristic form of PEDV grown in the presence of trypsin or elastase that seems to induce necrosis in cells at the end of viral replication. Thus, intensive necrosis of cell monolayers is seen at approximately 40-48 h following virus infection. This PEDV, passaged with GCDCA, can also grow in simple MEM in the absence of GCDCA (but CPE progress is slower without GCDCA) or in the presence of fetal bovine serum (FBS). Once completely adapted to the cell culture with GCDCA, virus no longer replicates well in the presence of trypsin (unlike elastase adapted PEDV) (Table 2 and FIG. 1), suggesting that growth of this virus may be attenuated in animals. Thus this enzyme-independent PEDV (8aa) would be an excellent candidate for both killed and attenuated vaccines. The limited growth of 8aa PEDV in the presence of trypsin was also confirmed by IFA and Western blot analysis (FIG. 2). The enzyme-independent virus (designated herein as "8aa") was deposited with the American Type Culture Collection, located at 10801 University Boulevard, Manassas, Va. 20110-2209, on Dec. 11, 2014, under the provisions of the Budapest Treaty, with ATCC Accession No. PTA-121847, which is hereby incorporated by reference.

Example 5. Antigenicity of Generated Strains

Real-time qRT-qPCR: PEDV RNA was extracted from the stool samples or cell culture following repeated freezing and thawing using the RNeasy Kit (Qiagen, Valencia, Calif.) according to the manufacturer protocol. Real-time qRT-PCR was performed by using One-Step Platinum qRT-PCR kit (Invitrogen, Carlsbad, Calif.) using the following primers and probe (-3') targeting the N gene:

```
                                         (SEQ ID NO: 4)
Forward primer    5'-TCTCGTAAGAGTCCGCTAGCTC-3'

(SEQ ID NO: 5)
Reverse primer    5'-GCTATGCTCAGATCGCCAGT-3'

(SEQ ID NO: 6)
Probe             5'-TGCTCTTTGGTGGTAATGTGGC-3'
```

The probe includes a 5' FAM™ dye (Applied Biosystems) with an internal ZEN Quencher (non-base modifier, positioned 9 bases from the 5' dye) and a 3' Iowa Black® Fluorescent Quencher (IABkFQ). The qRT-PCR amplification was performed in a Rotor-Gene Q (Qiagen) with the following conditions: 50° C. for 30 min and 95° C. for 5 min, then 30 cycles of denaturation at 95° C. for 15 sec, annealing at 60° C. for 60 sec and elongation at 72° C. for 30 s. The Ct values were converted to TCID50 equivalent/ml based on the equation derived from the standard curve generated with the serial dilution of cell culture-grown PEDV.

Western Blot: For Western blot analysis, confluent Vero cells grown in 6 well plates were infected with PEDV KD, PEDV AA or PEDV 8aa (2 MOI) in the presence of trypsin, elastase or GCDCA, respectively. Similarly, growth of PEDV 8aa with or without trypsin, elastase or GCDCA were also monitored by Western blot analysis. After 24 hr of virus infection, cell lysates were prepared for SDS-PAGE (12% Tris-glycine gel), and proteins were transferred to nitrocellulose membranes. Membranes were probed with the positive or negative pig sera followed by horseradish peroxidase-conjugated goat swine IgG antibody. Proteins were visualized by chemiluminescence (Thermo Scientific). Concentrated (×100) PEDV KD, PEDV AA or PEDV 8aa by ultracentrifugation (100,000×g for 2 hr in 30% sucrose cushion) were also examined with Western blot analysis. Serial dilution of each concentrated PEDV (1:5, 1:50 or 1:500) passage was prepared for SDS-PAGE for the Western blot analysis. Western blot analysis with elastase-adapted (AA) or enzyme-independent PEDV (8aa PEDV) or serum neutralization assay with trypsin-adapted (KD), elastase-adapted (AA) or enzyme-independent PEDV (8aa PEDV) against convalescent sera pooled from pigs infected with a US PEDV strain (day 43) demonstrated that antibodies in the sera from a US PEDV strain recognize viral proteins of KD, AA and 8aa (FIG. 3), indicating that those strains retain similar immunogenic epitopes, including neutralizing epitopes, from its parent KD strain and a US PEDV strain.

Immunofluorescence assay (IFA): For analysis of viral protein, confluent Vero cells grown in 96 well plates were infected with PEDV KD, PEDV AA or PEDV 8aa (2 MOI) in the presence of trypsin, elastase or GCDCA, respectively. After 24 hr of infection, cells were fixed with chilled methanol. For IFA, the positive or negative sera were added to the each well, followed by the incubation with FITC-conjugated goat anti-swine IgG. The plates were washed with PBS and visualized for fluorescence under a fluorescent microscope.

Antibody titrations and serum neutralization: To determine the IFA antibody titers against PEDV KD or PEDV 8aa in the pig serum samples, the virus infected cells were prepared by inoculating PEDV KD or PEDV 8aa to confluent Vero cells at a MOI of 1. The virus-infected cells were fixed with cold methanol after 24 hr-incubation at 37° C. in the presence of trypsin or GCDCA. Each serum sample was 2 or 10-fold diluted in PBS and 50 µl of the diluted sample was added to each well containing PEDV-infected cells. After 1 hr incubation at 37° C., cells were washed 3-times with PBS and FITC-conjugated rabbit anti-swine Ig was added to each well for staining. At 30 min after the staining, fluorescent signals in cells were observed by a fluorescent microscope. IFA titers were determined as the last dilution showing the fluorescent signals.

The serum neutralization assay (SN) was performed with the same convalescent sera (day 43) and trypsin-adapted (KD), elastase-adapted (AA) or enzyme-independent PEDV (8aa PEDV). The pooled sera was 2-fold diluted in MEM and mixed with the same volume (50 ul each) of each KD, AA or 8aa PEDV at 200 $TCID_{50}$ titer. The mixture was incubated in 37° C. for 30 min, then transferred to fresh Vero cells and incubated in the presence of trypsin (1-2 ug/ml) for KD or AA PEDV, or GCDCA (100 µM) for 8aa PEDV. Serum neutralization titers were determined by observing the appearance of CPE during the 3 days of incubation. Titers were determined as the reciprocal serum dilution of CPE inhibition. Repeated assays showed that titers were much more consistent with 8aa PEDV compared to KD or AA PEDV, which may be attributable to interference of serum with trypsin/elastase activities. The IFA or SN titers of the pooled sera were comparable against 8aa or KD PEDV at ~400 or ~80, respectively.

Example 6—Immune Responses to Piglets Inoculated with 8Aa PEDV P40

An animal study to determine immune responses to 8aa PEDV was conducted. Four, 4-day old, nursing piglets were inoculated with 8aa PEDV P40 $1 \times 10^6$ $TCID_{50}$ per animal via oral gavage. The piglets and adult pigs were penned together, such that the adult pigs became infected from PEDV shed from the piglets. Virus shedding as well as clinical symptoms including diarrhea from piglets occurred from about 3 day after virus inoculation. Serum samples were collected from each piglet and sow after 3 weeks. The collected serum samples were tested for IFA and SN titers against 8aa or KD PEDV. The SN test was performed using 8aa or KD PEDV in the presence of GCDCA (100 µM) or trypsin (1 µg/ml), respectively. The IFA titers of the serum from piglets were in the range of 400-1000, and the IFA titer for sow serum was 1500. The SN titers against 8aa or KD PEDV were comparable at 100-160 for piglet sera, and at ~200 for sow serum. These results suggest that 8aa PEDV induces good immune responses in young and adult pigs. Importantly, 8aa PEDV produced neutralizing antibodies to both 8aa and KD (trypsin-dependent) PEDV, which indicates that 8aa PEDV retains epitopes necessary for neutralizing the parental trypsin-growing PEDV virus isolated in the US and can be used for immunization.

To determine the pathogenicity (attenuation) of the PEDV generated with different methods, 1-4 day old newborn piglets from PEDV-negative sows housed in the farrowing crates were inoculated with PEDV KD (P154), PEDV AA (P103), PEDV 8aa (P40, P70 and P105), PEDV 8aa E10 or PEDV 8aa T5. Each PEDV was orally administrated to 1-4 day old neonatal piglets at $1 \times 10^6$ $TCID_{50}$ per animal. After inoculation, clinical symptoms, mortality (survival) and virus shedding (daily rectal swabs) were examined for up to 14 days. Virus shedding was examined by real time qRT-PCR as described above. Serum samples were collected from each piglet weekly and tested for IFA and SN titers against PEDV 8aa.

Example 7—Safety of KD (P154), AA (P103) or 8Aa PEDV (P105) in Neonatal Piglets (1-3-Day Old Piglets) by Oral Administration An animal study to determine the safety of KD (P154), AA (P103) or 8aa PEDV (P105) in neonatal piglets (1-3-day old piglets) by oral administration was conducted. Each strain was inoculated at $1 \times 10^6$ $TCID_{50}$ per animal via oral gavage, and clinical symptoms, mortality and virus shedding (daily rectal swabs) were examined for 10 days. In the group of pigs, KD strain (P154) was inoculated into six 1 day old piglets, and clinical symptoms, mortality and virus shedding (daily rectal swabs) were examined for 8 days. During the study period, virus shedding of $>1 \times 10^5$ $TCID_{50}$ was observed from 2-day post-virus inoculation and 60% mortality was observed in the KD group. This result indicates that KD PEDV was partly attenuated at the passage number 154. For AA PEDV (P103), three 1-day and twelve 2-day old piglets (total 15 animals) were inoculated with the strain. High virus shedding ($>1 \times 10^5$ $TCID_{50}$) was seen from 1-day post-virus inoculation and by day 10, 50% mortality was observed in the AA group. For 8aa PEDV (P105), nine 1-day and seven 2-day old piglets (total 16 animals) were inoculated with the strain. During that period, there was no evidence of diarrhea or mortality, and low levels of virus shedding ($<1 \times 10^2$ $TCID_{50}$) were observed for all piglets inoculated with 8aa. These results indicate that while AA PEDV was partly attenuated at the passage number 103, 8aa PEDV at the passage number 105 was fully attenuated in neonatal piglets.

Example 8—PEDV Challenge Studies

At 24 days-post virus inoculation of PEDV 8aa P70 or 8aa E10, animals (N=16 or 12, respectively) were challenged with a virulent wild type PEDV. The control animals (age-matched, PEDV-naive animals, N=10). After virus challenge, clinical symptoms and virus shedding (daily rectal swabs) were examined for up to 14 days. Serum samples were also collected from each piglet weekly, and they were tested for IFA and SN titers as described above.

Example 9—Sequencing Analysis of S Gene of the Trypsin-Adapted (KD), Elastase-Adapted (AA) or Enzyme-Independent (8Aa) PEDV The sequence analysis of the S gene of the trypsin-adapted (KD), elastase-adapted (AA) or enzyme-independent (8aa) PEDV showed that these are highly homologous to current US strains including Colorado strain, but also have minor mutations in the gene. More mutations were observed in elastase-adapted (AA) or enzyme-independent (8aa) PEDV, and these may be the result of the selection pressures by elastase or GCDCA.

(1) Enzyme-independent PEDV (8aa PEDV, P21) from Example 4. Amino acid sequence of S gene protein. (SEQ ID NO:1)

MKSLTYFWLFLPVLSTLSLPQDVTRCSANTNFRRFFSKFNVQAPAVVVLG
GYLPIGENQGVNSTWYCAGQHPTASGVHGIFVSHIRGGHGFEIGISQEPF
DPSGYQLYLHKATNGNTNATARLRICQFPSIKTLGPTANNDVTTGRNCLF
NKAIPAHMSEHSVVGITWDNDRVTVFSDKIYYFYFKNDWSRVATKCYNSG
GCAMQYVYEPTYYMLNVTSAGEDGISYQPCTANCIGYAANVFATEPNGHI
PEGFSFNNWFLLSNDSTLVHGKVVSNQPLLVNCLLAIPKIYGLGQFFSFN
QTIDGVCNGAAVQRAPEALRFNINDISVILAEGSIVLHTALGTNFSFVCS
NSSNPHLATFAIPLGATQVPYYCFFKVDTYNSTVYKFLAVLPPTVREIVI
TKYGDVYVNGFGYLHLGLLDAVTINFTGHGTDDDVSGFWTIASTNFVDAL
IEVQGTTIQRILYCDDPVSQLKCSQVAFDLDDGFYTISSRNLLSHEQPIS
FVTLPSFNDHSFVNITVSASFGGHSGANLIASDTTINGFSSFCVDTRQFT
ISLFYNVTNSYGYVSKSQDSNCPFTLQSVNDYLSFSKFCVSTSLLASACT
IDLFGYPEFGSGVKFTSLYFQFTKGELITGTPKPLEGVTDVSFMTLDVCT
KYTIYGFKGEGIITLTNSSFLAGVYYTSDSGQLLAFKNVTSGAVYSVTPC
SFSEQAAYVDDDIVGVISSLSSSTFNSTRELPGFFYHSNDGSNCTEPVLV
YSNIGVCKSGSIGYVPSQSGQVKIPPTVTGNISIPTNFSMSIRTEYLQLY
NTPVSVDCATYVCNGNSRCKQLLTQYTAACKTIESALQLSARLESVEVNS
MLTISDEALQLATISSFNGDGYNFTNVLGVSVYDPASGRVVQKRSFIEDL
LFNKVVTNGLGTVDEDYKRCSNGRSVADLVCAQYYSGVMVLPGVVDAEKL
HMYSASLTGGMVLGGFTSAAALPFSDAVQARLNYLALQTDVLQRNQQLLA
ESFNSAIGNITSAFESVKEAISQTSKGLNTVAHALTKVQEVVNSQGAALT
QLTVQLQHNFQAISSSIDDIYSRLDILSADAQVDRLITGRLSALNAFVAQ
TLTKYTEVQASRKLAQQKVNECVKSQSQRYGFCGGDGEHIFSLVQAAPQG
LLFLHTVLVPSDFVDVIAIAGLCVNDEIALTLREPGLVLFTHELQNHTAT
EYFVSSRRMFEPRKPTVSDFVQIESCVVTYVNLTRDQLPDVIPDYIDVNK
TLYEILASLPNRTGPSLPLDVFNATYLNLTGEIADLEQRSESLRNTTEEL
QSLIYNINNTLVDLEWLNRVETYIKWPWWVWLIIFIVLIFVVSLLVFCCI
STGCCGCCGCCCACFSGCCRGPRLQPYEVFEKVHVQ.

Comparison between 8aa P21 and Colorado strain (GenBank accession # KF272920.1):

Ten amino acid changes: T326I, L375F, A457T, P486T, A775P, E856D, I958T, Y976D, V1081A, D1253Y Colorado strain (GenBank accession # KF272920.1) vs classical European strain CV777 (GenBank accession # AF353511.1): approximately 90% identity.

(2) Trypsin-adapted PEDV (KD PEDV, P33) from Example 1 and 2. Amino acid sequence of S gene protein. (SEQ ID NO:2)

MKSLTYFWLFLPVLSTLSLPQDVTRCSANTNFRRFFSKFNVQAPAVVVLG
GYLPIGENQGVNSTWYCAGQHPTASGVHGIFVSHIRGGHGFEIGISQEPF
DPSGYQLYLHKATNGNTNATARLRICQFPSIKTLGPTANNDVTTGRNCLF
NKAIPAHMSEHSVVGITWDNDRVTVFSDKIYYFYFKNDWSRVATKCYNSG
GCAMQYVYEPTYYMLNVTSAGEDGISYQPCTANCIGYAANVFVTEPNGHI
PEGFSFNNWFLLSNDSTLVHGKVVSNQPLLVNCLLAIPKIYGLGQFFSFN
QTIDGVCNGAAVQRAPEALRFNINDTSVILAEGSIVLHTALGTNFSFVCS
NSSNPHLATFAIPLGATQVPYYCFLKVDTYNSTVYKFLAVLPPTVREIVI
TKYGDVYVNGFGYLHLGLLDAVTINFTGHGTDDDVSGFWTIASTNFVDAL
IEVQGTAIQRILYCDDPVSQLKCSQVAFDLDDGFYPISSRNLLSHEQPIS
FVTLPSFNDHSFVNITVSASFGDHSGANLIASDTTINGFSSFCVDTRQFT
ISLFYNVTNSYGYVSKSQDSNCPFTLQSVNDYLSFSKFCVSTSLLASACT
IDLFGYPEFGSGVKFTSLYFQFTKGELITGTPKPLEGVTDVSSMTLDVCT
KYTIYGFKGEGIITLTNSSFLAGVYYTSDSGQLLAFKNVTSGAVYSVTPC
SFSEQAAYVDDDIVGVISSLSSSTFNSTRELPGFFYHSNDGSNCTEPVLV
YSNIGVCKSGSIGYVPSQSGQVKIAPTVTGNISIPTNFSMSIRTEYLQLY
NTPVSVDCATYVCNGNSRCKQLLTQYTAACKTIESALQLSARLESVEVNS
MLTISEEALQLATISSFNGDGYNFTNVLGVSVYDPASGRVVQKRSFIEDL
LFNKVVTNGLGTVDEDYKRCSNGRSVADLVCAQYYSGVMVLPGVVDAEKL
HMYSASLIGGMVLGGFTSAAALPFSYAVQARLNYLALQTDVLQRNQQLLA
ESFNSAIGNITSAFESVKEAISQTSKGLNTVAHALTKVQEVVNSQGAALT
QLTVQLQHNFQAISSSIDDIYSRLDILSADVQVDRLITGRLSALNAFVAQ
TLTKYTEVQASRKLAQQKVNECVKSQSQRYGFCGGDGEHIFSLVQAAPQG
LLFLHTVLVPSDFVDVIAIAGLCVNDEIALTLREPGLVLFTHELQNHTAT
EYFVSSRRMFEPRKPTVSDFVQIESCVVTYVNLTRDQLPDVIPDYIDVNK
TLDEILASLPNRTGPSLPLDVFNATYLNLTGEIADLEQRSESLRNTTEEL
QSLIYNINNTLVDLEWLNRVETYIKWPWWVWLIIFIVLIFVVSLLVFCCI
STGCCGCCGCCCACFSGCCRGPRLQPYEVFEKVHVQ.

Comparison between KD P33 and Colorado strain (GenBank accession # KF272920.1):

Three amino acid changes in the S protein: all in S1 region, A243V, G523D, F643S.

(3) Elastase-adapted PEDV (AA PEDV, P17) from Example 3. Amino acid sequence of S gene protein. (SEQ ID NO:3)

MKSLTYFWLFLPVLSTLSLPQDVTRCSANTNFRRFFSKFNVQAPAVVVLG
GYLPIGENQGVNSTWYCAGQHPTASGVHGIFVSHIRGGHGFEIGISQEPF
DPSGYQLYLHKATNGNTNATARLRICQFPSIKTLGPTANNDVTTGRNCLF
NKAIPAHMSEHSVVGITWDNDRVTVFSDKIYYFYFKNDWSRVATKCYNSG
GCAMQYVYEPTYYMLNVTSAGEDGISYQPCTANCIGYAANVFVTEPNGHI
PEGFSFNNWFLLSNDSTLVHGKVVSNQPLLVNCLLAIPKIYGLGQFFSFN
QTIDGVCNGAAVQRAPEALRFNINDTSVILAEGSIVLHTALGTNFSFVCS
NSSNPHLATFAIPLGATQVPYYCFFKVDTYNSTVYKFLAVLPPTVREIVI
TKYGDVYVNGFGYLHLGLLDAVTINFTGHGTDDDVSGFWTIASTNFVDAL
IEVQGTAIQRILYCDDPVSQLKCSQVAFDLDDGFYTISSRNLLSHEQPIS

```
FVTLPSFNDHSFVNITVSASFGGHSGANLIASDTTINGFSSFCVDTRQFT

ISLFYNVTNSYGYVSKSXDSNCPFTLQSVNDYLSFSKFCVSTSLLASACT

IDLFGYPEFGSGVKFTSLYFQFTKGELITGTPKPLEGVTDVSFMTLDVCT

KYTIYGFKGEGIITLTNSSFLAGVYYTSDSGQLLAFKNVTSGAVYSVTPC

SFSEQAAYVDDDIVGVISSLSSSTFNSTRELPGFFYHSNDGSNCTEPVLV

YSNIGVCKSGSIGYVPSQSGQVKIAPTVTGNISIPTNFSMSIRTEYLQLY

NTPVSVDCATYVCNGNSRCKQLLTQYTAACKTIESALQLSARLESVEVNS

MLTISDEALQLATISSFNGDGYNFTNVLGVSVYDPASGRVVQKRSFIEDL

LFNKVVTNGLGTVDEDYKRCSNGRSVADLVCAQYYSGVMVLPGVVDAEKL

HMYSASLIGGMVLGGFTSAAALPFSYAVQARLNYLALQTDVLQRNQQLLA
```

-continued
```
ESFNSAIGNITSAFESVKEATSQTSKGLNTVAHALTKVQEVVNSQGAALT

QLTVQLQHKFQAISSSIDDIYSRLDILLADAQVDRLITGRLSALNAFVAQ

TLTKYTEVQASRKLAQQKVNECVKSQSQRYGFCGGDGEHIFSLVQAAPQG

LLFLHTVLVPSDFVDVIAIAGLCVNDEIALTLREPGLVLFTHELQNHTAT

EYFVSSRRMFEPRKPTVSDFVQIESCVVTYVNLTRDQLPDVIPDYIDVNK

TLDEILASLPNRTGPSLPLDVFNATYLNLTGEIADLEQRSESLRNTTEEL

QSLIYNINNTLVDLEWLNRVETYIKWPWWVWLIIFIVLIFVVSLLVFCCI

STGCCGCCGCCCACFSGCCRGPRLQPYEVFEKVHVQ.
```

Comparison between AA P17 and Colorado strain (GenBank accession #KF272920.1):

Seven amino acid changes: A243V, L375K, P486T, E856D, N1059K, S1078L, V1081A.

Results and Discussion

Cell Culture Adaptation.

Initial attempts to isolate the PEDV U.S. strain required 2-3 blind passages until apparent CPE appeared in Vero cells. Virus growth in cell culture was confirmed by IFA staining using the PEDV specific antisera, and sequencing of S gene of the virus revealed higher than 99% amino acid homology to that of Colorado US PEDV strain (GenBank: KF272920.1, incorporated by reference herein). After virus cloning with the limited dilution method, PEDV was further passaged under different culture conditions. In the presence of trypsin (1-2 μg/ml), after about 20 passages of the wild-type PEDV at 0.1-1 MOI, PEDV KD began to grow faster based on the apparent CPE appearance in 24 hr-post inoculation (PI), leading to complete cell lysis by 48 hr PI. Larger syncytia were also observed in cell monolayers. After passage number 20, PEDV KD titers consistently reached to 6.2-6.5 $\log_{10}$ TCID$_{50}$/ml (Table 1).

When the wild-type PEDV was passaged in the presence of elastase (1-2 μg/ml), apparent CPE was observed after 2-3 passages. This elastase-passaged virus (PEDV AA) grew well in the presence of either trypsin or elastase, but they showed higher titers when titration was done in the presence of trypsin in the media, compared to when titration was done with elastase (Table 1). For the first 20 passages in elastase, PEDV AA titers gradually increased and became consistent at 6.5-6.8 or 5.1-5.5 log 10 TCID$_{50}$/ml with trypsin or elastase, respectively. The viral titers of PEDV AA with trypsin were slightly higher than those of PEDV KD (Table 1).

TABLE 1

PEDV titers ($\log_{10}$ TCID$_{50}$/ml) which were determined in the presence of trypsin, elastase or GCDCA, as indicated.

| PEDV KD | | PEDV AA | | | PEDV 8aa | | |
|---|---|---|---|---|---|---|---|
| Passage No | Titration with Trypsin | Passage No | Titration with | | Passage No | Titration with | |
| | | | Trypsin | Elastase | | GCDCA | Trypsin |
| P4 | 5.1 | P4 | 3.8 | 2.5 | P4 | 2.5 | 3.1 |
| P10 | 5.8 | P10 | 5.2 | 4.1 | P14 | 6.6 | 5.1 |
| P20 | 6.3 | P20 | 6.7 | 5.3 | P17 | 7.5 | 2.2 |
| P30 | 6.2 | P30 | 6.5 | 5.1 | P21 | 8.1 | <2 |
| P40 | 6.5 | P40 | 6.7 | 5.5 | P30 | 8.2 | <2 |
| P60 | 6.2 | P60 | 6.8 | 5.3 | P70 | 8.2 | <2 |
| P120 | 6.3 | P120 | 6.7 | 5.2 | P120 | 8.1 | <2 |

In addition, adaptation of virus to propagate without any protease was achieved by passaging the wild-type PEDV in Vero cells (PEDV 8aa) in the presence of conjugated bile acids (GCDCA, 100 μM). PEDV 8aa started to efficiently grow after about 10 passages and virus growth did not form syncytium, which is a characteristic CPE observed in virus-infected cells in the presence of trypsin or elastase. Extensive cell death (necrosis) of cell monolayers infected with PEDV 8aa occurred at approximately 40-48 h following virus infection. Virus titers reached more than 8.0 log 10 TCID$_{50}$/ml after passage number 20 (Table 1), which are significantly higher than those of PEDV KD or PEDV AA (Table 1). Interestingly, after 10 passages of initial adaptation with GCDCA, PEDV 8aa was also able to grow in MEM in the absence of GCDCA or in the presence of fetal bovine serum (FBS). While CPE progressed more rapidly when GCDCA was present in the culture media, the titers of PEDV 8aa grown in GCDCA, MEM (without FBS) or MEM containing 2% FBS were comparable among them (FIG. 2).

Interestingly, once completely adapted to grow in the presence of GCDCA after passage number 20, the replication of PEDV 8aa became greatly inhibited by trypsin (Table 1 and FIG. 2); virus titers decreased to <2.0 log 10 TCID$_{50}$ ml (Table 1). The reduction in growth of 8aa PEDV (passage number 21) in the presence of trypsin was also confirmed by IFA and Western blot analysis (FIG. 1). From the IFA staining, few positive cells were observed in the cell culture infected with PEDV 8aa grown in the presence of trypsin (1 μg/ml), while a majority of cells were positively stained for PEDV in cell culture infected with PEDV 8aa grown in MEM containing GCDCA or mock (FIG. 1). By adding different concentrations of trypsin (0.01, 0.1 or 1 µg/ml) in the media, trypsin-dependent inhibition of the replication of PEDV 8aa was confirmed in the Western blot analysis: N protein levels were reduced at higher trypsin concentrations (FIG. 1).

Figure 3:
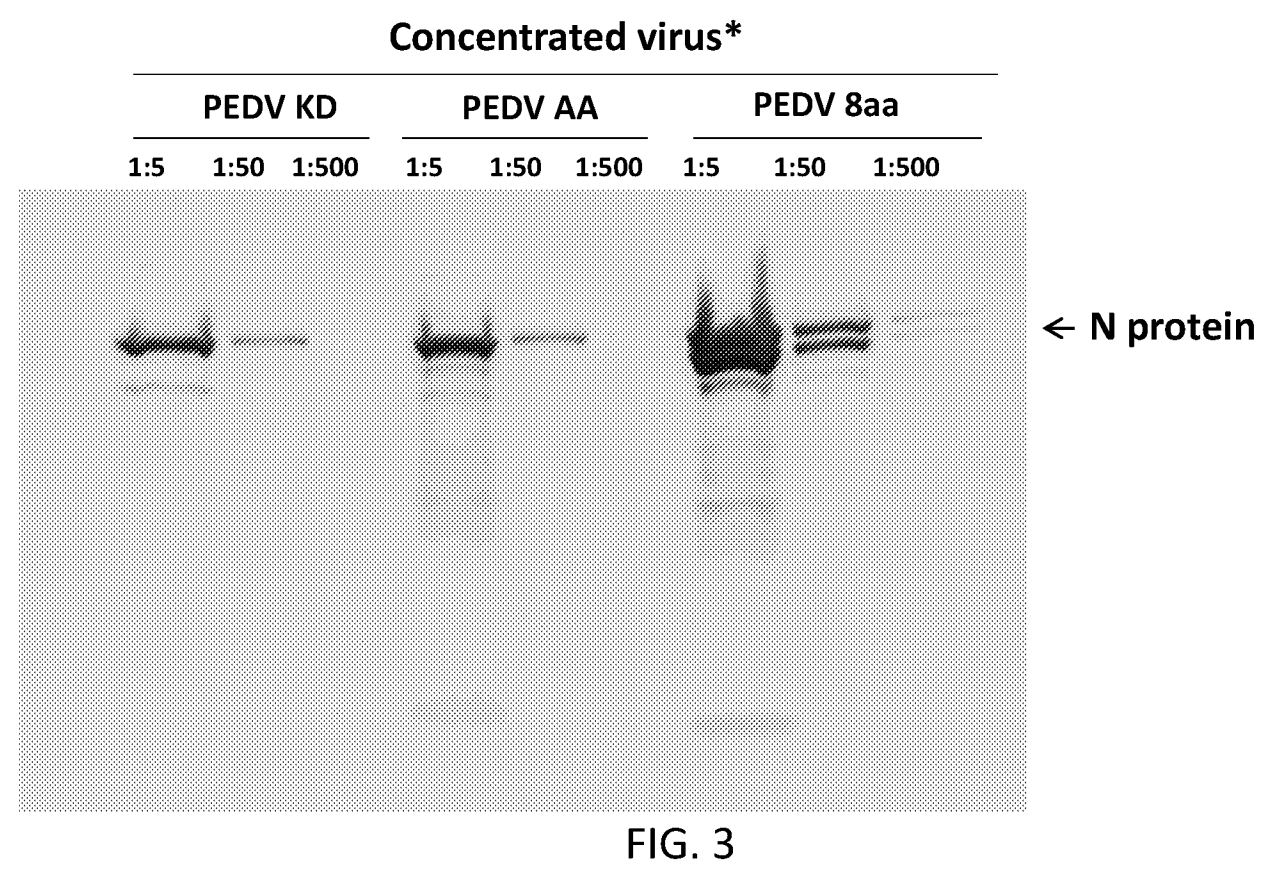

Western blot analysis on the concentrated PEDV KD, PEDV AA or PEDV 8aa against the convalescent sera pooled from pigs infected with a US PEDV strain (day 43) also demonstrated and confirmed higher levels of viral replication of PEDV 8aa compared to PEDV KD and AA (FIG. 3). The IFA or SN titers of PEDV KD or PEDV 8aa were comparable to each other; IFA titers of PEDV KD or PEDV 8aa were 1255±23 or 1243±31, respectively and SN titers of PEDV KD or PEDV 8aa were 48±16 or 52±4, respectively. These results indicate that both PEDV 8aa and KD strains retain cross-reactivity to the parental wild-type PEDV strain.

Pathogenicity of PEDV in Neonatal Piglets.

The results of the animal studies to determine the pathogenicity of PEDV KD, AA, 8aa (P40, P70 and P105), 8aa E10 and 8aa T5 in neonatal piglets are summarized in Table 2. Mortality varied among different virus inoculation groups from 0 to 100% (Table 1, FIGS. 3 and 4). The onset of duration of symptoms (diarrhea) and virus shedding also differed among groups (Table 1, FIGS. 4 and 5).

Figure 4:
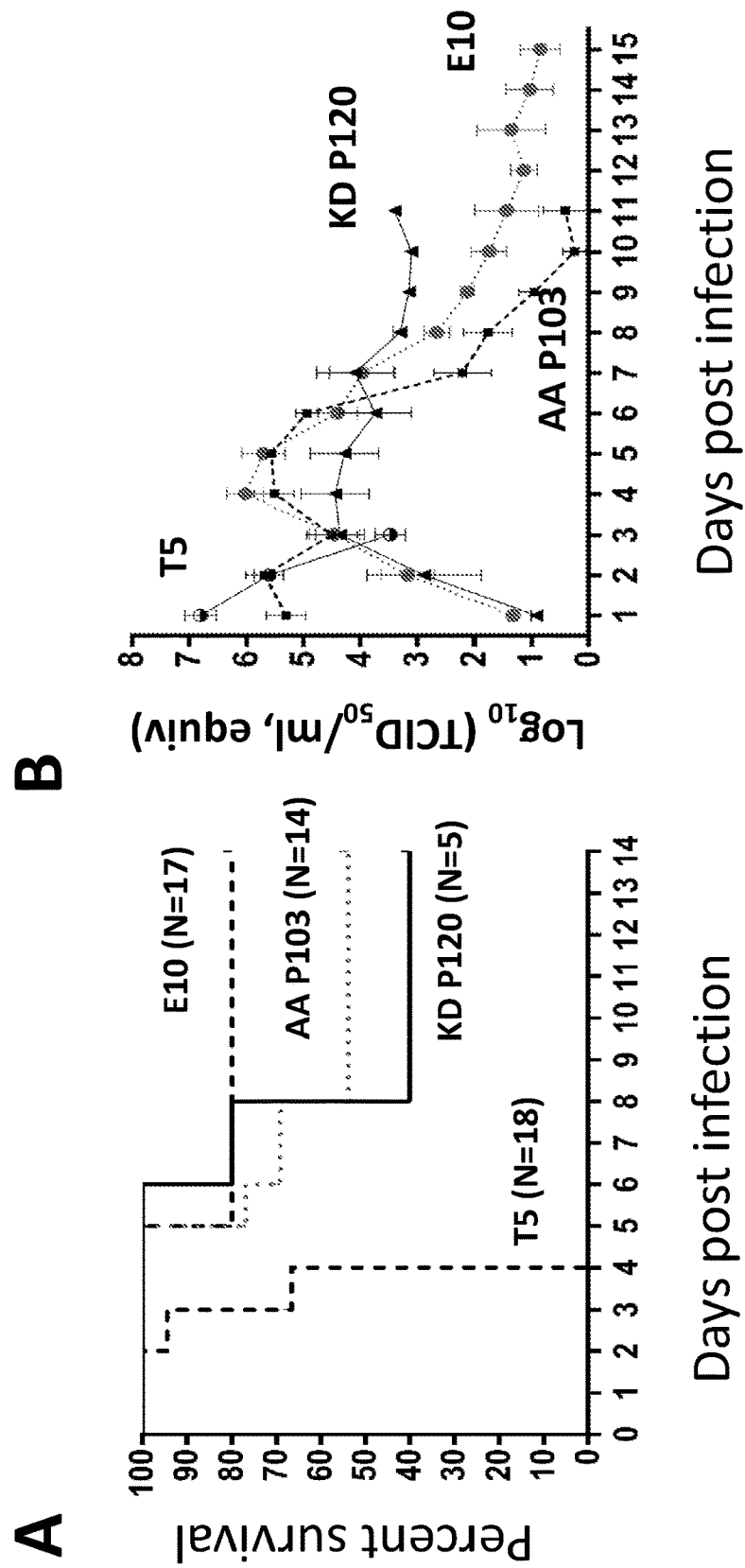
FIG. 4 shows graphs for: A. Survival curve; and B. Virus shedding after PEDV KD P120 (KD P120), PEDV AA P103 (AA P103), PEDV 8aa T5 (T5) or PEDV 8aa E10 (E10) were inoculated to 1-4 day old piglets.

In a group of 2-day old piglets inoculated with PEDV KD P120, four out of six piglets died during 6 to 8 days post-infection (DPI) (67% mortality). Virus shedding and diarrhea started at 2 and 3 DPI, respectively. Fecal viral titers reached to 4.5 log 10 $TCID_{50}$ equivalent/ml at 4 DPI and remained above 3-4 log 10 $TCID_{50}$ equivalent/ml until 11 DPI (end of observation) (FIG. 4). In a group of 2-day old piglets inoculated with PEDV AA P103, 7 out of 14 piglets died during 5 to 8 DPI (50% mortality) (Table 2 and FIG. 4). Virus shedding and diarrhea started at 1 and 2 DPI, respectively. Fecal viral titers reached to 5.2 and 5.5 log 10 $TCID_{50}$ equivalent/ml at 1 and 2 DPI, respectively and remained above 4-5 log 10 $TCID_{50}$ equivalent/ml at 6 DPI, which gradually reduced below 1 log 10 TCID50 equivalent/ml after 9 DPI (FIG. 4).

For a group of 1-day old piglets inoculated with PEDV 8aa E10, 5 out of 17 animals died during 5 to 7 DPI (29% mortality) (Table 1, FIG. 4). Virus shedding and diarrhea started at 2 and 3 DPI, respectively. Fecal viral titers reached to 6.0 log 10 $TCID_{50}$ equivalent/ml at 4 DPI, and gradually dropped below 2 log 10 TCID50 equivalent/ml after 9 DPI (FIG. 4). The 1-day old piglets infected with PEDV 8aa T5 all died by 4 DPI (100% mortality) (Table 1). In this group, high virus shedding and diarrhea started at 1 DPI, and fecal viral titers reached to 6.7 log 10 $TCID_{50}$ equivalent/ml at 1 DPI (FIG. 4).

Figure 5:
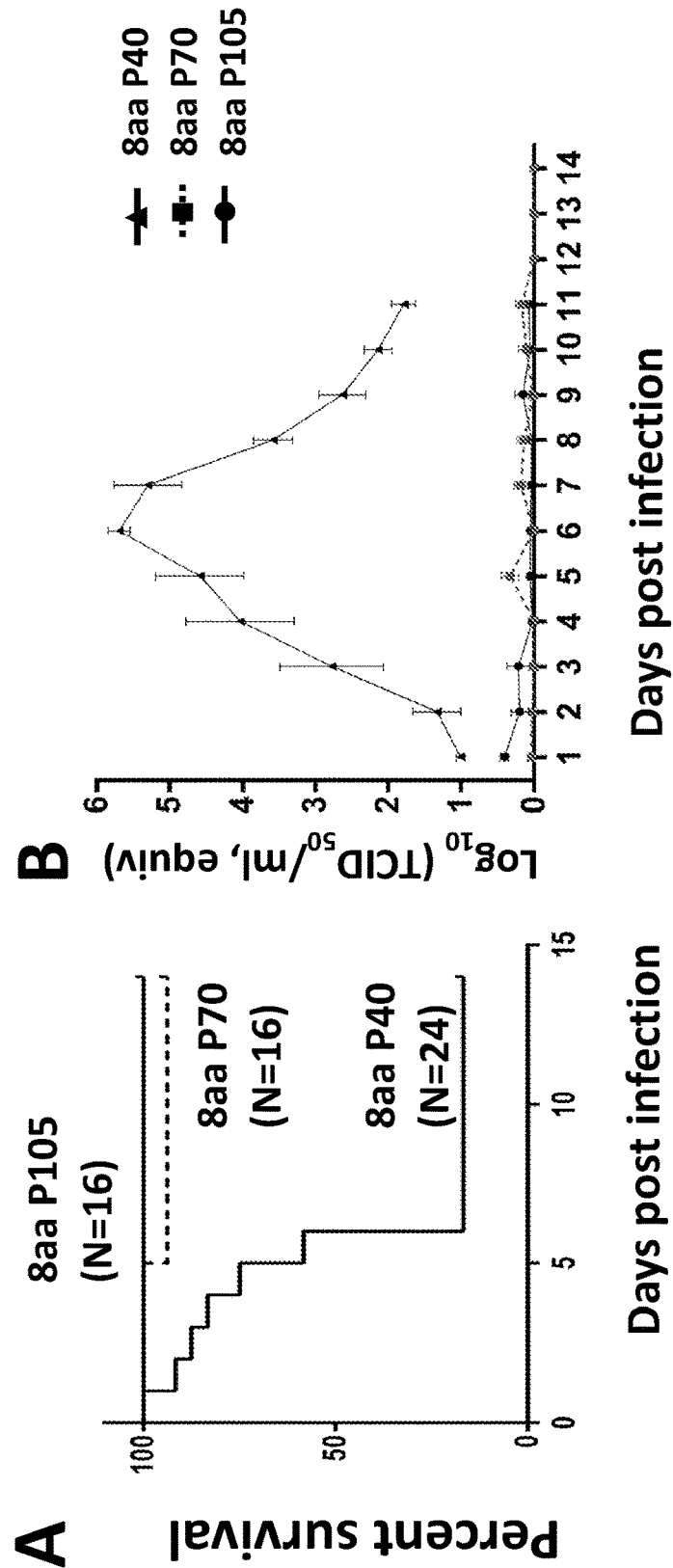
FIG. 5 shows graphs for: A. Survival curve; and B. Virus shedding after PEDV 8aa P40 (8aa P40), PEDV 8aa P70 (8aa P70) or PEDV 8aa P105 (8aa P105) were inoculated to 1-4 day old piglets.

The three groups inoculated with three different passage numbers (P40, P70 and P105) of PEDV 8aa were comprised of piglets at 1 day-old (P70), 1-2 day old (P105) or 2 or 4 day old (P40) at the time of virus inoculation (Table 1). Those piglets infected with PEDV 8aa P40 sustained high mortality during 2-8 DPI (83% mortality) with high viral shedding and diarrhea starting at 2 and 3 DPI, respectively (FIG. 5). In this group, the fecal viral titers reached to 7.0 log 10 $TCID_{50}$ equivalent/ml at 4 DPI and remained above 6-7 log 10 $TCID_{50}$ equivalent/ml until 8 DPI (FIG. 5). In contrast, the survival rate of the piglets and viral shedding/diarrhea indicate that PEDV 8aa became greatly attenuated after passage number 70 (P70). Inoculation of PEDV 8aa P70 or P105 led to only one death (6% mortality) or no mortality, respectively, even in 1 or 2 day-old piglets that are known to be highly susceptible to PEDV-caused mortality. The one pig died after inoculation of PEDV 8aa P70 seems to be not-related to PEDV as there was no clinical symptom or virus shedding (Table 2, FIG. 5). In some animals infected with PEDV 8aa P70, loose stool was observed at 1 and 2 DPI, which resolved after 2 DPI, and limited virus shedding (<1 log 10 $TCID_{50}$ equivalent/ml) was observed up to 15 DPI (FIG. 5). In the group of PEDV 8aa P105, no loose stool or diarrhea was observed and limited virus shedding (<1 log 10 $TCID_{50}$ equivalent/ml) was seen up to 13 DPI (FIG. 5).

Wild-Type Virus Challenge Study in Piglets Previously Infected with PEDV 8Aa P70 or 8Aa E10.

Those piglets inoculated with PEDV 8aa P70 or PEDV 8aa E10 in the previous pathogenicity study were used for this study. After 24 DPI, those piglets were challenged with a wild-type PEDV. Age-matched, PEDV-naïve piglets were also included in the study as a control group (Table 3).

TABLE 2

Summary of pathogenicity (attenuation) studies of PEDV KD, AA and 8aa at different passage numbers in 1-4 day old piglets.

| Group | Inoculum | Age at inoculation (numbers) | # of survived animals (mortality %) | Clinical symptoms and virus shedding |
|---|---|---|---|---|
| 1 | PEDV KD P120 | 2-day old (N = 6) | 2/6 (67%) | Diarrhea: 3-9 DPI; virus shedding started at 2 DPI |
| 2 | PEDV AA P103 | 2-day-old (N = 14) | 7/14 (50%) | Diarrhea: 2-9 DPI; virus shedding started at 1 DPI |
| 3 | PEDV 8aa E10 | 1-day old (N = 17) | 12/17 (29%) | Loose stool: 1-2 DPI; diarrhea 3-7 DPI; virus shedding started at 2 DPI |
| 4 | PEDV 8aa T5 | 1-day-old (N = 18) | 0/18 (100%) | Onset of diarrhea from 1 DPI; all died by 4 DPI; virus shedding from 1 DPI |
| 5 | PEDV 8aa P40 | 2 or 4-day old (N = 24) | 4/24 (83%) | Diarrhea: 3-8 DPI; virus shedding from 2 DPI |
| 6 | PEDV 8aa P70 | 1-day-old (N = 17) | 16/17 (6%) 1 died by accident | Loose stool at 1-2 DPI; limited virus shedding |
| 7 | PEDV 8aa P105 | 1- or 2-day old (N = 16) | 16/16 (0%) | No diarrhea; limited virus shedding |

TABLE 3

Summary of average SN titers and clinical symptoms (protection) in the challenge studies.

| Group | Virus inoculation (1-day-old) | Average of SN titers (DPI) | | | Challenge (24 days after virus inoculation) | Protection (Diarrhea; virus shedding) | Average of SN titers (DPI after challenge) | | | |
|---|---|---|---|---|---|---|---|---|---|---|
| | | 12 | 19 | 25 | | | 1 | 8 | 15 | 21 |
| 1 | PEDV 8aa P70 | <10 | <10 | <10 | Wild type PEDV | Diarrhea 3-4 DPI; virus shedding start at 2 DPI | <10 | 212.3 | 219.2 | 216.2 |
| 2 | PEDV 8aa E10 | 14.6 | 57.9 | 50.0 | Wild type PEDV | No diarrhea; limited virus shedding | 58.0 | 60.6 | 148.2 | 40.4 |
| 3 | N/A | N/A | N/A | N/A | Wild type PEDV | Diarrhea 3-4 DPI; virus shedding start at 2 DPI | <10 | 36.3 | 34.4 | 29.1 |

Figure 6:
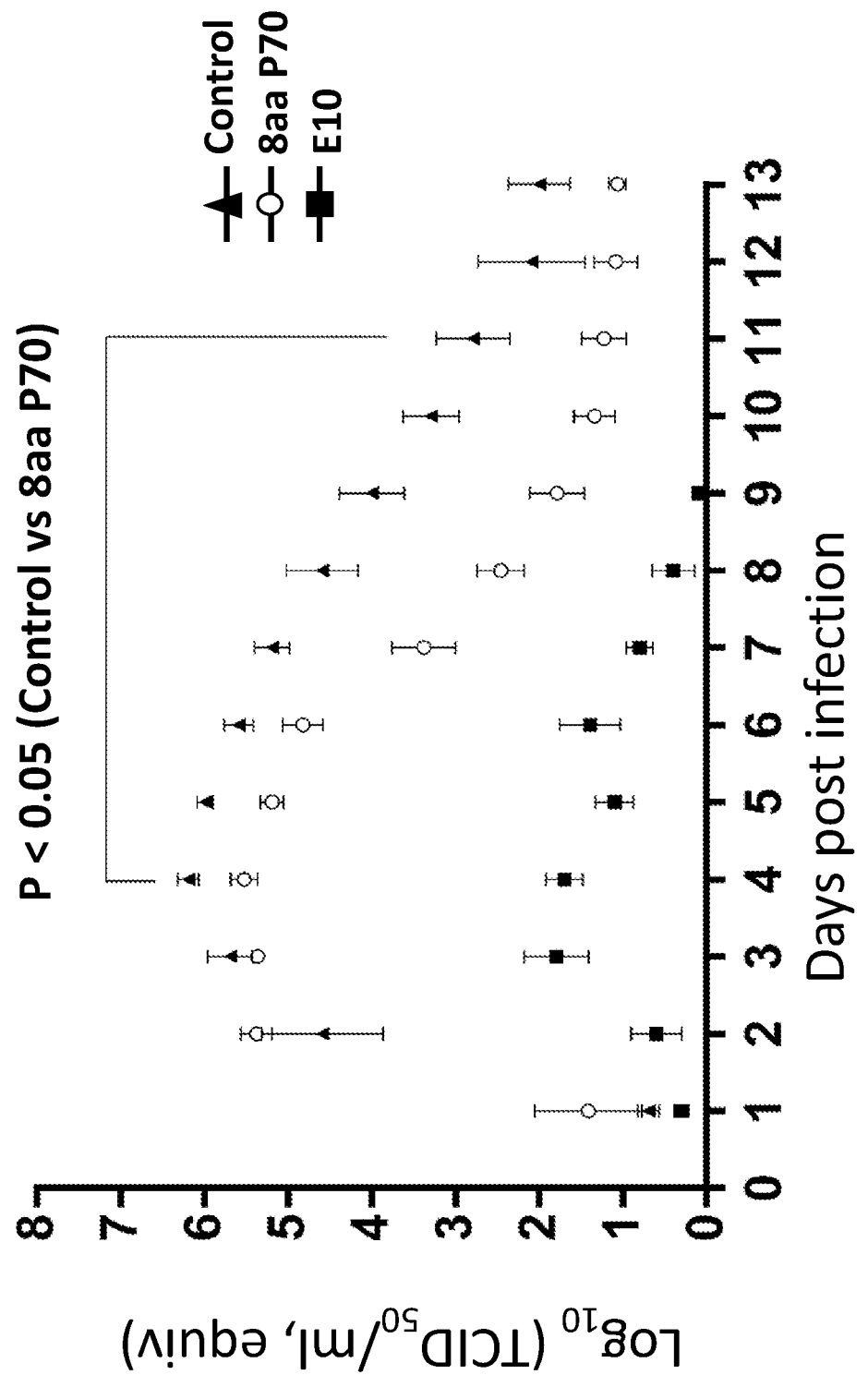
FIG. 6 shows a graph of the results for virus shedding after the challenges with wild type PEDV strain. The animals from FIG. 4 (PEDV E10) or FIG. 5 (PEDV P70) were challenged with wild type PEDV strain after 24 days of initial inoculation. Age-matched animals were also used for the challenge study as a control.

Following wild-type PEDV infection, no mortality was observed in all groups (Table 3). However, in the control and PEDV 8aa P70 groups, but not in PEDV 8aa E10 group, mild diarrhea was observed during 3 and 4 days post wild-type PEDV infection (Table 2). In PEDV 8aa E10 group, virus shedding was limited after wild-type virus infection. However, higher levels of virus shedding were observed in PEDV 8aa P70 and control groups, reaching up to 6.2 log 10 $TCID_{50}$ equivalent/ml at day 2-4 and gradually dropping to <3 log 10 $TCID_{50}$ equivalent/ml after day 11 of challenge. Interestingly, the virus titers of PEDV P70 group were significantly lower than those of control group during 4 and 11 days post challenge (FIG. 6).

Immunogenicity (SN Titers).

Figure 7:
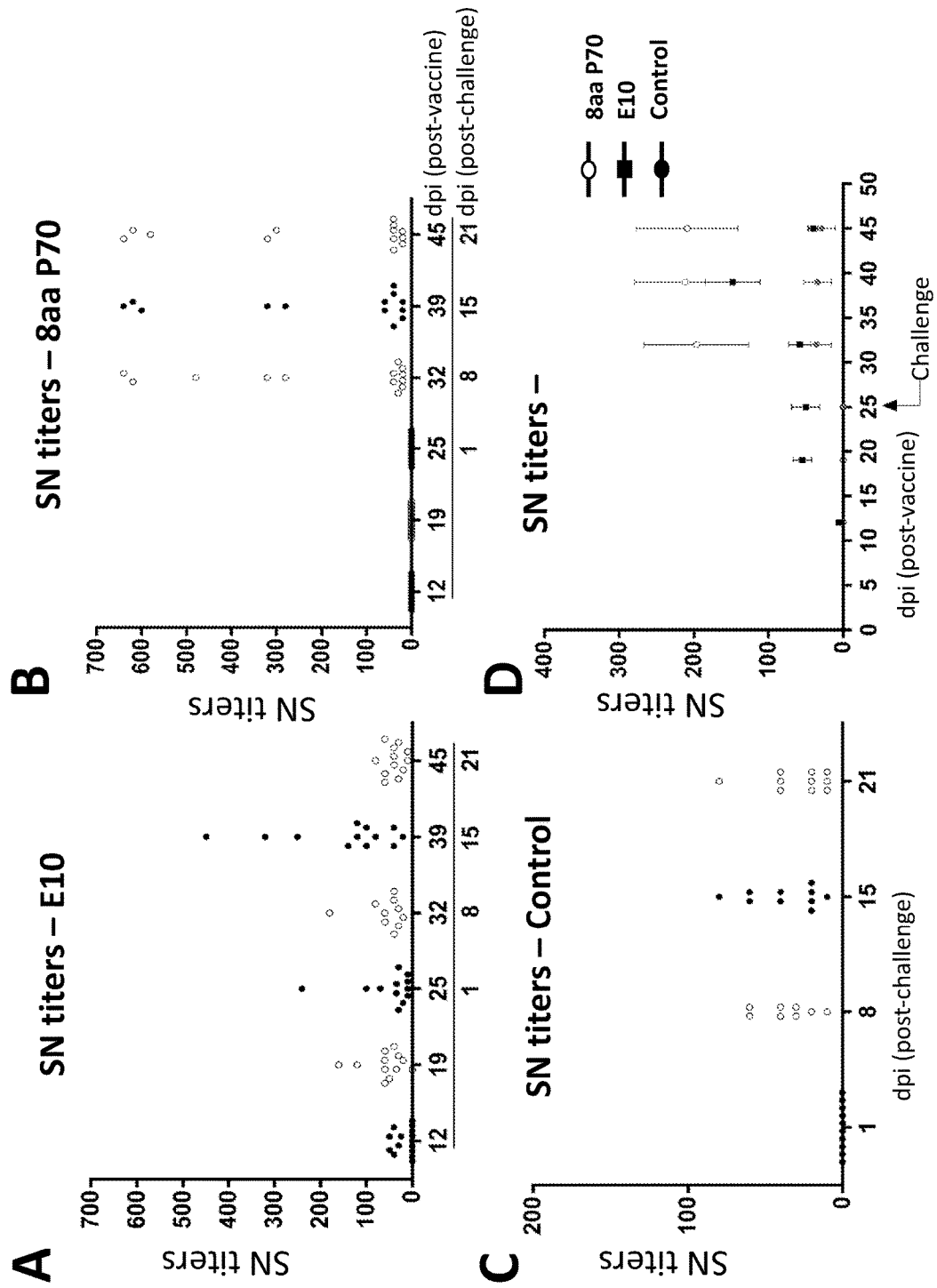
FIG. 7 shows graphs of serial SN titers in the animals in the challenge studies before and after the challenge with a wild-type PEDV. A-C: individual SN titers for PEDV 8aa E10, PEDV 8aa P70 or control group before (post-inoculation of each adapted PEDV strain) or after the challenge (post challenge). D: average SN titers of all groups before and after PEDV challenge.

Animals in the challenge studies (three groups) were monitored for serial SN titers before and after the wild-type PEDV challenge. Average SN titers were shown in Table 3 and FIG. 7D, and individual SN titers were shown in FIG. 7 A-C. The pigs in the control group were confirmed as PEDV-negative before the challenge (Table 3, FIG. 7). In the control group, SN titers were detected at 8 days post-challenge (average SN titer of 36.3) and remained steady for up to 21 day-post challenge (Table 3, FIG. 7). In PEDV 8aa E10 group, SN titers were detected at 12 days after the initial infection of PEDV 8aa E10, which increased over time prior to challenge (Table 3, FIG. 7). After the challenge, average SN titers peaked at 15 day post challenge (148.2) and dropped (Table 3, FIG. 7). In PEDV 8aa P70 group, no SN titers were detected prior to challenge (Table 3, FIG. 7). However, average titers reached >200 at day 8-21 post challenge. Interestingly, in this group, about 40% of animals showed high SN titers over 250 (anamnestic immune responses) and other animals developed limited SN titers (<50) (FIG. 7B).

Discussion

The PEDV strains circulating in the Asia belong to subgroup 1 and, in those countries, MLVs have been used for the control of PEDV. The US PEDV strains have approximately 10% diversity compared to subgroup 1 and are phylogenetically grouped in subgroup 2a. The heterogeneity of PEDV US suggests that there may be limited cross-reactivity between the US and Asian strains, which would require the development of specific vaccines for PEDV US strains for effective PEDV control in the US. For the production of killed vaccines or MLV, generation of PEDV to high titers in cell culture is highly important. However, propagation of PEDV to high titers (>8 log 10 $TCID_{50}$/ml) is not easily achieved. In this study, to generate PEDV US strains with properties suitable for vaccine production, we investigated the effects of various selective pressure in changing viral growth characteristics by serially-passaging our PEDV US isolate n in cell culture. In conventional culture of PEDV, trypsin, which is present at high concentrations in the small intestines, is required for isolation and propagation in cell culture. In our study, we also passaged PEDV in the presence of trypsin to generate PEDV KD strain. Once adapted well in Vero cells, PEDV KD induced typical and extensive cell fusion with syntitium with rapid progress of CPE, leading to death of all monolyed cells by 48 hr post-infection even at a low MOI (<0.05). This PEDV KD, after passage number 10, yielded titers of 5.8-6.5 log 10 $TCID_{50}$/ml (Table 1), similar to those reported by other groups. The presence of trypsin in virus propagation tend to yield inconsistent viral titers, observation made by us and others, possibly due to the inherent variation in progression of CPE of syntisum formation. Therefore, we sought to generate viruses that do not require trypsin for viral propagation.

Elastase is a proteolytic enzyme produced by pancreas (elastase 1) or neutrophils (elastase 2) and involved in catalyzing the breakdown of elastin, or bacteria during inflammation in the lung, respectively. Elastase recognizes the carboxyl groups of small hydrophobic amino acid such as glycine, alanine and valine for the proteolytic activity. Using this enzyme, PEDV AA passages were obtained. It took 3-5 passages (from the initial isolate with trypsin) to efficient replication in elastase (1 µg/ml), and once adapted well (after passage number 10), virus infection induced extensive fusion similar to PEDV KD, and complete CPE progress by 48 hr with even low MOI (<0.05) infections. While PEDV KD can grow well with only trypsin (not with elastase), PEDV AA passages can grow well with both trypsin and elastase, and they can be titrated with either trypsin or elastase. The titers reached to 6.8 log 10 $TCID_{50}$/ml when titration was done with trypsin, which is slightly higher than PEDV KD passages. However, when PEDV AA was titered in the presence of elastase, the titers were approximately 10-fold lower than those with trypsin (Table 1). Antigenic masses between PEDV KD or PEDV AA were similar when they were assessed with Western blot analysis after each virus was concentrated at the same ratio (FIG. 3).

Bile acids are synthesized in the liver, and stored in the gallbladder (as high as 320 mM). Their release into the duodenum is triggered primarily in response to the presence of dietary fat, and the bile concentrations in the upper small intestines can reach >1 mM. While the bile acids travel through the intestinal tracts, most of them (>95%) are reabsorbed into the blood system (through the portal vein)

and to the liver by passive diffusion or active mechanisms with the specific bile acid transporters in the intestine. Once returned to the liver, bile acids are to be re-released to the duodenum (enterohepatic circulation of bile acids). This circulation is essential in maintaining an effective concentration of bile acids and cholesterol homeostasis. We and other group have shown that bile acids can influence the replication of various viruses which target bile rich organs (liver and intestines) including porcine enteric calicivirus, hepatitis B and C virus and rotaviruses. Because PEDV also targets small intestines, we tested if bile acids can modulate the PEDV replication by passaging the virus in the presence of GCDCA.

PEDV 8aa were gradually adapted in the condition (GCDCA 100 and eventually it was able to grow high viral titers with up to 8.2 log 10 $TCID_{50}$/ml (Table 1). Furthermore once it was fully adapted in the condition, PEDV 8aa can grow in simple MEM without any supplement or in the presence of FBS (FIG. 1). Unlike PEDV KD or PEDV AA, PEDV 8aa induced the CPE without fusion and extensive cell death (necrosis) occurred during 24-48 hr after virus infection. Interestingly, during the early passage numbers (between passage 4 to 20), PEDV 8aa gradually lost its ability to grow in the presence of trypsin (Table 1). After passage number 20 the growth of PEDV 8aa is severely reduced to <2 log 10 $TCID_{50}$/ml in the presence of trypsin (or elastase) (Table 1), suggesting potential attenuation in animals because PEDV replication occur in intestines with high concentrations of trypsin (or elastase). The lack of viral growth in the presence of trypsin was also confirmed with IFA and Western blot analysis (FIG. 2). In addition to high titers of this virus, due to the independency of this virus on enzymes in cell culture, viral titers was more consistent compared to those of PEDV KD or AA.

Western blot analysis or SN assay with PEDV KD, PEDV AA, PEDV 8aa passages against the convalescent sera suggested that these PEDV passages retain similar immunogenic epitopes including neutralizing epitopes. The IFA or SN titers of the pooled sera were comparable against PEDV KD, PEDV AA or PEDV 8aa. We found that using PEDV 8aa for SN titration has clear advantage over PEDV KD or PEDV AA with much more consistent titers with multiple serum samples. These may be due to interference of serum samples with trypsin/elastase activities in the assay with PEDV KD or PEDV AA.

An animal study to determine the pathogenicity (attenuation) of PEDV KD (P154), PEDV AA (P103) or PEDV 8aa (P40, P70 and P105), PEDV 8aa E10, PEV 8aa T5 in neonatal piglets (1-4 day old piglets) by oral administration was conducted. The mortality was between 0 to 100% with these various PEDV passages, and virus shedding and clinical symptoms were well correlated in these studies (Table 2, FIGS. 4 and 5). It was shown that approximate 100 passages of PEDV in Vero cells may result in the attenuation in piglets, which is excellent candidate for MLVs. In this study, however, we found that PEDV KD or PEDV AA at the passage number over 100 still remained virulence (Table 2, FIG. 4), although some evidence for partial attenuation. For PEDV 8aa passages, while the passage number 40 (P40) was partially attenuated, both P70 and P105 were fully attenuated in the neonatal piglets (Table 2, FIG. 5). For PEDV 8aa P70 and P105, there was limited virus shedding with transient diarrhea (P70) or no clinical symptoms (P105) even at the most susceptible ages (1 day old piglets) (Table 2, FIG. 5). Interestingly, when the attenuated PEDV 8aa was adapted again in elastase (PEDV 8aa E10) and then trypsin (PEDV 8aa T5), they gained the virulence with 29% and 100% mortality, respectively (Table 2, FIG. 4). Virus shedding was observed from both PEDV 8aa E10 and PEDV 8aa T5 inoculated piglets, starting at day 2 and day 1, respectively (Table 2, FIG. 4). These results suggest that growth inhibition of PEDV 8aa in trypsin or elastase was a key for the fully attenuated phenomenon of PEDV 8aa passages in piglets. Currently, we are examining the mechanism for the growth restriction of PEDV 8aa in trypsin or elastase) in cell culture.

To evaluate the protection against wild type PEDV and active immune responses, animals survived from the inoculation of PEDV 8aa P70 or PEDV 8aa E10 were challenged with wild type PEDV after 24 days of initial inoculation. Age-matched animals were also challenged with wild type PEDV as a control group. Immune responses (SN titers) were also monitored before and after the challenge. Overall, immune responses (SN titers) and protection against the challenge were well correlated with prior clinical symptoms showing the animals with diarrhea with high virus shedding (PEDV 8aa E10) developed higher immune responses before challenge and greater protection against the challenge than animals with limited diarrhea and virus shedding (PEDV 8aa P70) (Table 3, FIG. 7).

After challenge, while the control animals and animals exposed to PEDV 8aa developed virus shedding from day 2 with transient diarrhea at day 3 and 4, there was significant different (p<0.05) in virus shedding during day 4 to 11 between the groups (FIG. 6). This difference suggests that animals exposed to PEDV 8aa P70 resolved the PEDV infections faster than the control animals. Interestingly, there were anamnestic immune responses (SN titers) in some animals exposed to PEDV 8aa P70 after the challenge (FIG. 7). About 40% of animals in the group developed and remained high SN titers after 1 week of challenge (FIG. 7), suggesting immune prime during the first infection. However, it is not clear why only less than half of animals in the group developed the anamnestic responses. It is possible that the infection levels were different among the animals from initial infection with PEDV 8aa P70 at the dose of 6 log 10 $TCID_{50}$/animal. Based on the attenuation in neonatal piglets, and fast resolution of virus shedding as well as anamnestic immune responses after the challenge, we conclude that PEDV 8aa P70 (and P105) is an excellent candidate for MLVs for emerging US PEDV. Currently we plan to examine PEDV 8aa P70 (or P105) in the passive protective immunity in pregnant sows and neonatal piglets.

The sequence analysis of S gene from trypsin-adapted (KD), elastase-adapted (AA) or enzyme-independent PEDV (8aa PEDV) KD, AA) or enzyme-independent (8aa) PEDV showed that these are highly homologous (>99%) to the current US strains including Colorado strain.

We claim:

1. A live, attenuated porcine epidemic diarrhea virus (PEDV) strain generated by serial passage in culture of an isolated PEDV strain deposited under ATCC Accession No. PTA-121847.

2. The attenuated PEDV of claim 1, wherein said attenuated PEDV strain results from serial passage in culture of said isolated PEDV strain deposited under ATCC Accession No. PTA-121847 at least thirty times for a total of at least 70 passages.

3. The attenuated PEDV of claim 1, wherein said attenuated PEDV strain results from subsequent passage in culture of said isolated PEDV strain deposited under ATCC Accession No. PTA-121847 at least sixty five times for a total of at least 105 passages.

4. The attenuated PEDV of claim 1, wherein said culture is substantially free of trypsin.

5. The attenuated PEDV of claim 1, wherein said culture is substantially free of elastase.

6. The attenuated PEDV of claim 1, wherein said culture comprises minimum essential medium or fetal bovine serum, and optionally conjugated bile acid.

7. The attenuated PEDV of claim 6, wherein said conjugated bile acid is glycochenodeoxycholic acid.

8. The attenuated PEDV of claim 1, wherein said live, attenuated PEDV strain is enzyme-independent.

9. The attenuated PEDV of claim 1, wherein said live, attenuated PEDV strain is trypsin- or elastase-independent.

10. An immunogenic composition comprising a live, attenuated PEDV according to claim 1, dispersed in a pharmaceutically-acceptable carrier.

11. The immunogenic composition of claim 10, said composition comprising at least about $1 \times 10^6$ $TCID_{50}$/ml attenuated PEDV per unit dose.

12. The immunogenic composition of claim 10 said composition further comprising a pharmaceutically-acceptable ingredient selected from the group consisting of adjuvants, additional antigens, buffering agents, salts, stabilizing agents, diluents, preservatives, antibiotics, isotonic agents, cell media, and mixtures thereof.

13. The immunogenic composition of claim 10, wherein said carrier is selected from the group consisting of water, normal saline, phosphate buffered saline, dextrose, oil-in-water emulsion, water-in-oil emulsion, dimethyl sulfoxide, ethanol, glycerol, and mixtures thereof.

14. A method of reducing the incidence of or reducing the severity of clinical symptoms of PEDV in a subject, said method comprising administering to the subject an immunogenic composition comprising a live, attenuated PEDV according to claim 1, dispersed in a pharmaceutically-acceptable carrier.

15. The method of claim 14, wherein said clinical symptoms are selected from the group consisting of loose stool, viral shedding, diarrhea, weight loss, anorexia, lethargy, and/or mortality.

16. The method of claim 14, wherein said subject is a pregnant animal, wherein offspring subsequently born by said animal have reduced incidence or severity of clinical symptoms of PEDV in comparison to offspring born by an animal not receiving the immunogenic composition.

17. The method of claim 14, wherein said immunogenic composition is administered orally or intramuscularly.

18. The method of claim 14, wherein said clinical symptoms are reduced in animals receiving the immunogenic composition by at least 10% in comparison to animals not receiving the immunogenic composition.

19. A kit for inducing an immune response against PEDV infection in a subject, said kit comprising:
an immunogenic composition comprising a live, attenuated PEDV according to claim 1; and
instructions for administering said immunogenic composition to said subject.

20. A method of inducing an immune response against PEDV infection in a subject comprising administering an immunogenic composition comprising a live, attenuated PEDV according to claim 1 to said subject.

* * * * *

SEQUENCE LISTING

<160> NUMBER OF SEQ ID NOS: 6

<210> SEQ ID NO 1
<211> LENGTH: 1386
<212> TYPE: PRT
<213> ORGANISM: porcine epidemic diarrhea virus

<400> SEQUENCE: 1

```
Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
210                 215                 220

Ile Ser Tyr Gln Pro Cys Thr Ala Asn Cys Ile Gly Tyr Ala Ala Asn
225                 230                 235                 240

Val Phe Ala Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
290                 295                 300

Gly Val Cys Asn Gly Ala Ala Val Gln Arg Ala Pro Glu Ala Leu Arg
305                 310                 315                 320

Phe Asn Ile Asn Asp Ile Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365
```

```
Val Pro Tyr Tyr Cys Phe Phe Lys Val Asp Thr Tyr Asn Ser Thr Val
    370                 375                 380

Tyr Lys Phe Leu Ala Val Leu Pro Pro Thr Val Arg Glu Ile Val Ile
385                 390                 395                 400

Thr Lys Tyr Gly Asp Val Tyr Val Asn Gly Phe Gly Tyr Leu His Leu
                405                 410                 415

Gly Leu Leu Asp Ala Val Thr Ile Asn Phe Thr Gly His Gly Thr Asp
                420                 425                 430

Asp Asp Val Ser Gly Phe Trp Thr Ile Ala Ser Thr Asn Phe Val Asp
            435                 440                 445

Ala Leu Ile Glu Val Gln Gly Thr Thr Ile Gln Arg Ile Leu Tyr Cys
450                 455                 460

Asp Asp Pro Val Ser Gln Leu Lys Cys Ser Gln Val Ala Phe Asp Leu
465                 470                 475                 480

Asp Asp Gly Phe Tyr Thr Ile Ser Ser Arg Asn Leu Leu Ser His Glu
                485                 490                 495

Gln Pro Ile Ser Phe Val Thr Leu Pro Ser Phe Asn Asp His Ser Phe
                500                 505                 510

Val Asn Ile Thr Val Ser Ala Ser Phe Gly Gly His Ser Gly Ala Asn
            515                 520                 525

Leu Ile Ala Ser Asp Thr Thr Ile Asn Gly Phe Ser Ser Phe Cys Val
530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Gln Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
        595                 600                 605

Phe Gly Ser Gly Val Lys Phe Thr Ser Leu Tyr Phe Gln Phe Thr Lys
    610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
                660                 665                 670

Gly Val Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
        690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
                740                 745                 750

Asn Ile Gly Val Cys Lys Ser Gly Ser Ile Gly Tyr Val Pro Ser Gln
            755                 760                 765

Ser Gly Gln Val Lys Ile Pro Pro Thr Val Thr Gly Asn Ile Ser Ile
        770                 775                 780

Pro Thr Asn Phe Ser Met Ser Ile Arg Thr Glu Tyr Leu Gln Leu Tyr
```

-continued

```
            785                 790                 795                 800
Asn Thr Pro Val Ser Val Asp Cys Ala Thr Tyr Val Cys Asn Gly Asn
                    805                 810                 815

Ser Arg Cys Lys Gln Leu Leu Thr Gln Tyr Thr Ala Ala Cys Lys Thr
                    820                 825                 830

Ile Glu Ser Ala Leu Gln Leu Ser Ala Arg Leu Glu Ser Val Glu Val
                    835                 840                 845

Asn Ser Met Leu Thr Ile Ser Asp Glu Ala Leu Gln Leu Ala Thr Ile
            850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                    885                 890                 895

Ile Glu Asp Leu Leu Phe Asn Lys Val Val Thr Asn Gly Leu Gly Thr
                    900                 905                 910

Val Asp Glu Asp Tyr Lys Arg Cys Ser Asn Gly Arg Ser Val Ala Asp
                    915                 920                 925

Leu Val Cys Ala Gln Tyr Tyr Ser Gly Val Met Val Leu Pro Gly Val
            930                 935                 940

Val Asp Ala Glu Lys Leu His Met Tyr Ser Ala Ser Leu Thr Gly Gly
945                 950                 955                 960

Met Val Leu Gly Gly Phe Thr Ser Ala Ala Ala Leu Pro Phe Ser Asp
                    965                 970                 975

Ala Val Gln Ala Arg Leu Asn Tyr Leu Ala Leu Gln Thr Asp Val Leu
                    980                 985                 990

Gln Arg Asn Gln Gln Leu Leu Ala  Glu Ser Phe Asn Ser  Ala Ile Gly
                    995                 1000                1005

Asn Ile  Thr Ser Ala Phe Glu  Ser Val Lys Glu Ala  Ile Ser Gln
            1010                1015                1020

Thr Ser Lys Gly Leu Asn Thr  Val Ala His Ala Leu  Thr Lys Val
            1025                1030                1035

Gln Glu Val Val Asn Ser Gly  Ala Ala Leu Thr  Gln Leu Thr
            1040                1045                1050

Val Gln Leu Gln His Asn Phe  Gln Ala Ile Ser Ser  Ser Ile Asp
            1055                1060                1065

Asp Ile  Tyr Ser Arg Leu Asp  Ile Leu Ser Ala Asp  Ala Gln Val
            1070                1075                1080

Asp Arg  Leu Ile Thr Gly Arg  Leu Ser Ala Leu Asn  Ala Phe Val
            1085                1090                1095

Ala Gln  Thr Leu Thr Lys Tyr  Thr Glu Val Gln Ala  Ser Arg Lys
            1100                1105                1110

Leu Ala  Gln Gln Lys Val Asn  Glu Cys Val Lys Ser  Gln Ser Gln
            1115                1120                1125

Arg Tyr  Gly Phe Cys Gly Gly  Asp Gly Glu His Ile  Phe Ser Leu
            1130                1135                1140

Val Gln  Ala Ala Pro Gln Gly  Leu Leu Phe Leu His  Thr Val Leu
            1145                1150                1155

Val Pro  Ser Asp Phe Val Asp  Val Ile Ala Ile Ala  Gly Leu Cys
            1160                1165                1170

Val Asn  Asp Glu Ile Ala Leu  Thr Leu Arg Glu Pro  Gly Leu Val
            1175                1180                1185

Leu Phe  Thr His Glu Leu Gln  Asn His Thr Ala Thr  Glu Tyr Phe
            1190                1195                1200
```

-continued

Val Ser Ser Arg Arg Met Phe Glu Pro Arg Lys Pro Thr Val Ser
1205                1210                1215

Asp Phe Val Gln Ile Glu Ser Cys Val Val Thr Tyr Val Asn Leu
1220                1225                1230

Thr Arg Asp Gln Leu Pro Asp Val Ile Pro Asp Tyr Ile Asp Val
1235                1240                1245

Asn Lys Thr Leu Tyr Glu Ile Leu Ala Ser Leu Pro Asn Arg Thr
1250                1255                1260

Gly Pro Ser Leu Pro Leu Asp Val Phe Asn Ala Thr Tyr Leu Asn
1265                1270                1275

Leu Thr Gly Glu Ile Ala Asp Leu Glu Gln Arg Ser Glu Ser Leu
1280                1285                1290

Arg Asn Thr Thr Glu Glu Leu Gln Ser Leu Ile Tyr Asn Ile Asn
1295                1300                1305

Asn Thr Leu Val Asp Leu Glu Trp Leu Asn Arg Val Glu Thr Tyr
1310                1315                1320

Ile Lys Trp Pro Trp Trp Val Trp Leu Ile Ile Phe Ile Val Leu
1325                1330                1335

Ile Phe Val Val Ser Leu Leu Val Phe Cys Cys Ile Ser Thr Gly
1340                1345                1350

Cys Cys Gly Cys Cys Gly Cys Cys Ala Cys Phe Ser Gly Cys
1355                1360                1365

Cys Arg Gly Pro Arg Leu Gln Pro Tyr Glu Val Phe Glu Lys Val
1370                1375                1380

His Val Gln
1385

<210> SEQ ID NO 2
<211> LENGTH: 1386
<212> TYPE: PRT
<213> ORGANISM: porcine epidemic diarrhea virus

<400> SEQUENCE: 2

Met Lys Ser Leu Thr Tyr Phe Trp Leu Phe Leu Pro Val Leu Ser Thr
1               5                   10                  15

Leu Ser Leu Pro Gln Asp Val Thr Arg Cys Ser Ala Asn Thr Asn Phe
                20                  25                  30

Arg Arg Phe Phe Ser Lys Phe Asn Val Gln Ala Pro Ala Val Val Val
            35                  40                  45

Leu Gly Gly Tyr Leu Pro Ile Gly Glu Asn Gln Gly Val Asn Ser Thr
50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe

-continued

```
                165                 170                 175
Ser Asp Lys Ile Tyr Tyr Phe Tyr Phe Lys Asn Asp Trp Ser Arg Val
                180                 185                 190
Ala Thr Lys Cys Tyr Asn Ser Gly Gly Cys Ala Met Gln Tyr Val Tyr
                195                 200                 205
Glu Pro Thr Tyr Tyr Met Leu Asn Val Thr Ser Ala Gly Glu Asp Gly
            210                 215                 220
Ile Ser Tyr Gln Pro Cys Thr Ala Asn Cys Ile Gly Tyr Ala Ala Asn
225                 230                 235                 240
Val Phe Val Thr Glu Pro Asn Gly His Ile Pro Glu Gly Phe Ser Phe
                245                 250                 255
Asn Asn Trp Phe Leu Leu Ser Asn Asp Ser Thr Leu Val His Gly Lys
                260                 265                 270
Val Val Ser Asn Gln Pro Leu Leu Val Asn Cys Leu Leu Ala Ile Pro
                275                 280                 285
Lys Ile Tyr Gly Leu Gly Gln Phe Phe Ser Phe Asn Gln Thr Ile Asp
            290                 295                 300
Gly Val Cys Asn Gly Ala Ala Val Gln Arg Ala Pro Glu Ala Leu Arg
305                 310                 315                 320
Phe Asn Ile Asn Asp Thr Ser Val Ile Leu Ala Glu Gly Ser Ile Val
                325                 330                 335
Leu His Thr Ala Leu Gly Thr Asn Phe Ser Phe Val Cys Ser Asn Ser
                340                 345                 350
Ser Asn Pro His Leu Ala Thr Phe Ala Ile Pro Leu Gly Ala Thr Gln
                355                 360                 365
Val Pro Tyr Tyr Cys Phe Leu Lys Val Asp Thr Tyr Asn Ser Thr Val
            370                 375                 380
Tyr Lys Phe Leu Ala Val Leu Pro Pro Thr Val Arg Glu Ile Val Ile
385                 390                 395                 400
Thr Lys Tyr Gly Asp Val Tyr Val Asn Gly Phe Gly Tyr Leu His Leu
                405                 410                 415
Gly Leu Leu Asp Ala Val Thr Ile Asn Phe Thr Gly His Gly Thr Asp
                420                 425                 430
Asp Asp Val Ser Gly Phe Trp Thr Ile Ala Ser Thr Asn Phe Val Asp
                435                 440                 445
Ala Leu Ile Glu Val Gln Gly Thr Ala Ile Gln Arg Ile Leu Tyr Cys
            450                 455                 460
Asp Asp Pro Val Ser Gln Leu Lys Cys Ser Gln Val Ala Phe Asp Leu
465                 470                 475                 480
Asp Asp Gly Phe Tyr Pro Ile Ser Ser Arg Asn Leu Leu Ser His Glu
                485                 490                 495
Gln Pro Ile Ser Phe Val Thr Leu Pro Ser Phe Asn Asp His Ser Phe
            500                 505                 510
Val Asn Ile Thr Val Ser Ala Ser Phe Gly Asp His Ser Gly Ala Asn
            515                 520                 525
Leu Ile Ala Ser Asp Thr Thr Ile Asn Gly Phe Ser Ser Phe Cys Val
            530                 535                 540
Asp Thr Arg Gln Phe Thr Ile Ser Leu Phe Tyr Asn Val Thr Asn Ser
545                 550                 555                 560
Tyr Gly Tyr Val Ser Lys Ser Gln Asp Ser Asn Cys Pro Phe Thr Leu
                565                 570                 575
Gln Ser Val Asn Asp Tyr Leu Ser Phe Ser Lys Phe Cys Val Ser Thr
                580                 585                 590
```

-continued

Ser Leu Leu Ala Ser Ala Cys Thr Ile Asp Leu Phe Gly Tyr Pro Glu
            595                 600                 605

Phe Gly Ser Gly Val Lys Phe Thr Ser Leu Tyr Phe Gln Phe Thr Lys
610                 615                 620

Gly Glu Leu Ile Thr Gly Thr Pro Lys Pro Leu Glu Gly Val Thr Asp
625                 630                 635                 640

Val Ser Ser Met Thr Leu Asp Val Cys Thr Lys Tyr Thr Ile Tyr Gly
                645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
            690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
                725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
            755                 760                 765

Ser Gly Gln Val Lys Ile Ala Pro Thr Val Thr Gly Asn Ile Ser Ile
770                 775                 780

Pro Thr Asn Phe Ser Met Ser Ile Arg Thr Glu Tyr Leu Gln Leu Tyr
785                 790                 795                 800

Asn Thr Pro Val Ser Val Asp Cys Ala Thr Tyr Val Cys Asn Gly Asn
                805                 810                 815

Ser Arg Cys Lys Gln Leu Leu Thr Gln Tyr Thr Ala Ala Cys Lys Thr
            820                 825                 830

Ile Glu Ser Ala Leu Gln Leu Ser Ala Arg Leu Glu Ser Val Glu Val
            835                 840                 845

Asn Ser Met Leu Thr Ile Ser Glu Glu Ala Leu Gln Leu Ala Thr Ile
850                 855                 860

Ser Ser Phe Asn Gly Asp Gly Tyr Asn Phe Thr Asn Val Leu Gly Val
865                 870                 875                 880

Ser Val Tyr Asp Pro Ala Ser Gly Arg Val Val Gln Lys Arg Ser Phe
                885                 890                 895

Ile Glu Asp Leu Leu Phe Asn Lys Val Thr Asn Gly Leu Gly Thr
            900                 905                 910

Val Asp Glu Asp Tyr Lys Arg Cys Ser Asn Gly Arg Ser Val Ala Asp
            915                 920                 925

Leu Val Cys Ala Gln Tyr Tyr Ser Gly Val Met Val Leu Pro Gly Val
            930                 935                 940

Val Asp Ala Glu Lys Leu His Met Tyr Ser Ala Ser Leu Ile Gly Gly
945                 950                 955                 960

Met Val Leu Gly Gly Phe Thr Ser Ala Ala Leu Pro Phe Ser Tyr
                965                 970                 975

Ala Val Gln Ala Arg Leu Asn Tyr Leu Ala Leu Gln Thr Asp Val Leu
            980                 985                 990

Gln Arg Asn Gln Gln Leu Leu Ala  Glu Ser Phe Asn Ser  Ala Ile Gly
            995                 1000                1005

-continued

```
Asn Ile Thr Ser Ala Phe Glu Ser Val Lys Glu Ala Ile Ser Gln
    1010                1015                1020

Thr Ser Lys Gly Leu Asn Thr Val Ala His Ala Leu Thr Lys Val
    1025                1030                1035

Gln Glu Val Val Asn Ser Gln Gly Ala Ala Leu Thr Gln Leu Thr
    1040                1045                1050

Val Gln Leu Gln His Asn Phe Gln Ala Ile Ser Ser Ser Ile Asp
    1055                1060                1065

Asp Ile Tyr Ser Arg Leu Asp Ile Leu Ser Ala Asp Val Gln Val
    1070                1075                1080

Asp Arg Leu Ile Thr Gly Arg Leu Ser Ala Leu Asn Ala Phe Val
    1085                1090                1095

Ala Gln Thr Leu Thr Lys Tyr Thr Glu Val Gln Ala Ser Arg Lys
    1100                1105                1110

Leu Ala Gln Gln Lys Val Asn Glu Cys Val Lys Ser Gln Ser Gln
    1115                1120                1125

Arg Tyr Gly Phe Cys Gly Gly Asp Gly Glu His Ile Phe Ser Leu
    1130                1135                1140

Val Gln Ala Ala Pro Gln Gly Leu Leu Phe Leu His Thr Val Leu
    1145                1150                1155

Val Pro Ser Asp Phe Val Asp Val Ile Ala Ile Ala Gly Leu Cys
    1160                1165                1170

Val Asn Asp Glu Ile Ala Leu Thr Leu Arg Glu Pro Gly Leu Val
    1175                1180                1185

Leu Phe Thr His Glu Leu Gln Asn His Thr Ala Thr Glu Tyr Phe
    1190                1195                1200

Val Ser Ser Arg Arg Met Phe Glu Pro Arg Lys Pro Thr Val Ser
    1205                1210                1215

Asp Phe Val Gln Ile Glu Ser Cys Val Val Thr Tyr Val Asn Leu
    1220                1225                1230

Thr Arg Asp Gln Leu Pro Asp Val Ile Pro Asp Tyr Ile Asp Val
    1235                1240                1245

Asn Lys Thr Leu Asp Glu Ile Leu Ala Ser Leu Pro Asn Arg Thr
    1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Ala Cys Phe Ser Gly Cys
    1355                1360                1365

Cys Arg Gly Pro Arg Leu Gln Pro Tyr Glu Val Phe Glu Lys Val
    1370                1375                1380

His Val Gln
    1385
```

```
<210> SEQ ID NO 3
<211> LENGTH: 1386
<212> TYPE: PRT
<213> ORGANISM: porcine epidemic diarrhea virus
<220> FEATURE:
<221> NAME/KEY: misc_feature
<222> LOCATION: (568)..(568)
<223> OTHER INFORMATION: Xaa can be any naturally occurring amino acid

<400> SEQUENCE: 3

Met Lys Ser Leu Thr Tyr Phe Trp Leu Phe Leu Pro Val Leu Ser Thr
 1               5                  10                  15

Leu Ser Leu Pro Gln Asp Val Thr Arg Cys Ser Ala Asn Thr Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ile Gly Glu Asn Gln Gly Val Asn Ser Thr
    50                  55                  60

Trp Tyr Cys Ala Gly Gln His Pro Thr Ala Ser Gly Val His Gly Ile
65                  70                  75                  80

Phe Val Ser His Ile Arg Gly Gly His Gly Phe Glu Ile Gly Ile Ser
                85                  90                  95

Gln Glu Pro Phe Asp Pro Ser Gly Tyr Gln Leu Tyr Leu His Lys Ala
            100                 105                 110

Thr Asn Gly Asn Thr Asn Ala Thr Ala Arg Leu Arg Ile Cys Gln Phe
        115                 120                 125

Pro Ser Ile Lys Thr Leu Gly Pro Thr Ala Asn Asn Asp Val Thr Thr
    130                 135                 140

Gly Arg Asn Cys Leu Phe Asn Lys Ala Ile Pro Ala His Met Ser Glu
145                 150                 155                 160

His Ser Val Val Gly Ile Thr Trp Asp Asn Asp Arg Val Thr Val Phe
                165                 170                 175

Ser Asp Lys Ile Tyr Tyr Phe Tyr Phe Lys Asn Asp Trp Ser Arg Val
            180                 185                 190

Ala Thr Lys Cys Tyr Asn Ser Gly Gly Cys Ala Met Gln Tyr Val Tyr
        195                 200                 205

Glu Pro Thr Tyr Tyr Met Leu Asn Val Thr Ser Ala Gly Glu Asp Gly
    210                 215                 220

Ile Ser Tyr Gln Pro Cys Thr Ala Asn Cys Ile Gly Tyr Ala Ala Asn
225                 230                 235                 240

Val Phe Val Thr Glu Pro Asn Gly His Ile Pro Glu Gly Phe Ser Phe
                245                 250                 255

Asn Asn Trp Phe Leu Leu Ser Asn Asp Ser Thr Leu Val His Gly Lys
            260                 265                 270

Val Val Ser Asn Gln Pro Leu Leu Val Asn Cys Leu Leu Ala Ile Pro
        275                 280                 285

Lys Ile Tyr Gly Leu Gly Gln Phe Phe Ser Phe Asn Gln Thr Ile Asp
    290                 295                 300

Gly Val Cys Asn Gly Ala Ala Val Gln Arg Ala Pro Glu Ala Leu Arg
305                 310                 315                 320

Phe Asn Ile Asn Asp Thr Ser Val Ile Leu Ala Glu Gly Ser Ile Val
                325                 330                 335

Leu His Thr Ala Leu Gly Thr Asn Phe Ser Phe Val Cys Ser Asn Ser
            340                 345                 350

Ser Asn Pro His Leu Ala Thr Phe Ala Ile Pro Leu Gly Ala Thr Gln
        355                 360                 365
```

```
Val Pro Tyr Tyr Cys Phe Phe Lys Val Asp Thr Tyr Asn Ser Thr Val
    370             375                 380

Tyr Lys Phe Leu Ala Val Leu Pro Pro Thr Val Arg Glu Ile Val Ile
385             390                 395                 400

Thr Lys Tyr Gly Asp Val Tyr Val Asn Gly Phe Gly Tyr Leu His Leu
            405                 410                 415

Gly Leu Leu Asp Ala Val Thr Ile Asn Phe Thr Gly His Gly Thr Asp
            420                 425                 430

Asp Asp Val Ser Gly Phe Trp Thr Ile Ala Ser Thr Asn Phe Val Asp
        435                 440                 445

Ala Leu Ile Glu Val Gln Gly Thr Ala Ile Gln Arg Ile Leu Tyr Cys
    450                 455                 460

Asp Asp Pro Val Ser Gln Leu Lys Cys Ser Gln Val Ala Phe Asp Leu
465                 470                 475                 480

Asp Asp Gly Phe Tyr Thr Ile Ser Ser Arg Asn Leu Leu Ser His Glu
            485                 490                 495

Gln Pro Ile Ser Phe Val Thr Leu Pro Ser Phe Asn Asp His Ser Phe
            500                 505                 510

Val Asn Ile Thr Val Ser Ala Ser Phe Gly Gly His Ser Gly Ala Asn
    515                 520                 525

Leu Ile Ala Ser Asp Thr Thr Ile Asn Gly Phe Ser Ser Phe Cys Val
    530                 535                 540

Asp Thr Arg Gln Phe Thr Ile Ser Leu Phe Tyr Asn Val Thr Asn Ser
545                 550                 555                 560

Tyr Gly Tyr Val Ser Lys Ser Xaa Asp Ser Asn Cys Pro Phe Thr Leu
                565                 570                 575

Gln Ser Val Asn Asp Tyr Leu Ser Phe Ser Lys Phe Cys Val Ser Thr
            580                 585                 590

Ser Leu Leu Ala Ser Ala Cys Thr Ile Asp Leu Phe Gly Tyr Pro Glu
    595                 600                 605

Phe Gly Ser Gly Val Lys Phe Thr Ser Leu Tyr Phe Gln Phe Thr Lys
610                 615                 620

Gly Glu Leu Ile Thr Gly Thr Pro Lys Pro Leu Glu Gly Val Thr Asp
625                 630                 635                 640

Val Ser Phe Met Thr Leu Asp Val Cys Thr Lys Tyr Thr Ile Tyr Gly
            645                 650                 655

Phe Lys Gly Glu Gly Ile Ile Thr Leu Thr Asn Ser Ser Phe Leu Ala
            660                 665                 670

Gly Val Tyr Tyr Thr Ser Asp Ser Gly Gln Leu Leu Ala Phe Lys Asn
            675                 680                 685

Val Thr Ser Gly Ala Val Tyr Ser Val Thr Pro Cys Ser Phe Ser Glu
    690                 695                 700

Gln Ala Ala Tyr Val Asp Asp Ile Val Gly Val Ile Ser Ser Leu
705                 710                 715                 720

Ser Ser Ser Thr Phe Asn Ser Thr Arg Glu Leu Pro Gly Phe Phe Tyr
            725                 730                 735

His Ser Asn Asp Gly Ser Asn Cys Thr Glu Pro Val Leu Val Tyr Ser
            740                 745                 750

Asn Ile Gly Val Cys Lys Ser Gly Ser Ile Gly Tyr Val Pro Ser Gln
    755                 760                 765

Ser Gly Gln Val Lys Ile Ala Pro Thr Val Thr Gly Asn Ile Ser Ile
770                 775                 780
```

```
Pro Thr Asn Phe Ser Met Ser Ile Arg Thr Glu Tyr Leu Gln Leu Tyr
785             790             795             800

Asn Thr Pro Val Ser Val Asp Cys Ala Thr Tyr Val Cys Asn Gly Asn
        805             810             815

Ser Arg Cys Lys Gln Leu Leu Thr Gln Tyr Thr Ala Ala Cys Lys Thr
        820             825             830

Ile Glu Ser Ala Leu Gln Leu Ser Ala Arg Leu Glu Ser Val Glu Val
            835             840             845

Asn Ser Met Leu Thr Ile Ser Asp Glu Ala Leu Gln Leu Ala Thr Ile
    850             855             860

Ser Ser Phe Asn Gly Asp Gly Tyr Asn Phe Thr Asn Val Leu Gly Val
865             870             875             880

Ser Val Tyr Asp Pro Ala Ser Gly Arg Val Val Gln Lys Arg Ser Phe
            885             890             895

Ile Glu Asp Leu Leu Phe Asn Lys Val Val Thr Asn Gly Leu Gly Thr
            900             905             910

Val Asp Glu Asp Tyr Lys Arg Cys Ser Asn Gly Arg Ser Val Ala Asp
        915             920             925

Leu Val Cys Ala Gln Tyr Tyr Ser Gly Val Met Val Leu Pro Gly Val
930             935             940

Val Asp Ala Glu Lys Leu His Met Tyr Ser Ala Ser Leu Ile Gly Gly
945             950             955             960

Met Val Leu Gly Gly Phe Thr Ser Ala Ala Ala Leu Pro Phe Ser Tyr
                965             970             975

Ala Val Gln Ala Arg Leu Asn Tyr Leu Ala Leu Gln Thr Asp Val Leu
            980             985             990

Gln Arg Asn Gln Gln Leu Leu Ala Glu Ser Phe Asn Ser Ala Ile Gly
        995             1000            1005

Asn Ile Thr Ser Ala Phe Glu Ser Val Lys Glu Ala Ile Ser Gln
    1010            1015            1020

Thr Ser Lys Gly Leu Asn Thr Val Ala His Ala Leu Thr Lys Val
    1025            1030            1035

Gln Glu Val Val Asn Ser Gln Gly Ala Ala Leu Thr Gln Leu Thr
    1040            1045            1050

Val Gln Leu Gln His Lys Phe Gln Ala Ile Ser Ser Ser Ile Asp
    1055            1060            1065

Asp Ile Tyr Ser Arg Leu Asp Ile Leu Leu Ala Asp Ala Gln Val
    1070            1075            1080

Asp Arg Leu Ile Thr Gly Arg Leu Ser Ala Leu Asn Ala Phe Val
    1085            1090            1095

Ala Gln Thr Leu Thr Lys Tyr Thr Glu Val Gln Ala Ser Arg Lys
    1100            1105            1110

Leu Ala Gln Gln Lys Val Asn Glu Cys Val Lys Ser Gln Ser Gln
    1115            1120            1125

Arg Tyr Gly Phe Cys Gly Gly Asp Gly Glu His Ile Phe Ser Leu
    1130            1135            1140

Val Gln Ala Ala Pro Gln Gly Leu Leu Phe Leu His Thr Val Leu
    1145            1150            1155

Val Pro Ser Asp Phe Val Asp Val Ile Ala Ile Ala Gly Leu Cys
    1160            1165            1170

Val Asn Asp Glu Ile Ala Leu Thr Leu Arg Glu Pro Gly Leu Val
    1175            1180            1185
```

```
Leu Phe Thr His Glu Leu Gln Asn His Thr Ala Thr Glu Tyr Phe
    1190                1195                1200

Val Ser Ser Arg Arg Met Phe Glu Pro Arg Lys Pro Thr Val Ser
    1205                1210                1215

Asp Phe Val Gln Ile Glu Ser Cys Val Val Thr Tyr Val Asn Leu
    1220                1225                1230

Thr Arg Asp Gln Leu Pro Asp Val Ile Pro Asp Tyr Ile Asp Val
    1235                1240                1245

Asn Lys Thr Leu Asp Glu Ile Leu Ala Ser Leu Pro Asn Arg Thr
    1250                1255                1260

Gly Pro Ser Leu Pro Leu Asp Val Phe Asn Ala Thr Tyr Leu Asn
    1265                1270                1275

Leu Thr Gly Glu Ile Ala Asp Leu Glu Gln Arg Ser Glu Ser Leu
    1280                1285                1290

Arg Asn Thr Thr Glu Glu Leu Gln Ser Leu Ile Tyr Asn Ile Asn
    1295                1300                1305

Asn Thr Leu Val Asp Leu Glu Trp Leu Asn Arg Val Glu Thr Tyr
    1310                1315                1320

Ile Lys Trp Pro Trp Trp Val Trp Leu Ile Ile Phe Ile Val Leu
    1325                1330                1335

Ile Phe Val Val Ser Leu Leu Val Phe Cys Cys Ile Ser Thr Gly
    1340                1345                1350

Cys Cys Gly Cys Cys Gly Cys Cys Cys Ala Cys Phe Ser Gly Cys
    1355                1360                1365

Cys Arg Gly Pro Arg Leu Gln Pro Tyr Glu Val Phe Glu Lys Val
    1370                1375                1380

His Val Gln
    1385

<210> SEQ ID NO 4
<211> LENGTH: 22
<212> TYPE: DNA
<213> ORGANISM: Artificial Sequence
<220> FEATURE:
<223> OTHER INFORMATION: Synthetic forward primer

<400> SEQUENCE: 4
tctcgtaaga gtccgctagc tc                                              22

<210> SEQ ID NO 5
<211> LENGTH: 20
<212> TYPE: DNA
<213> ORGANISM: Artificial Sequence
<220> FEATURE:
<223> OTHER INFORMATION: Synthetic reverse primer

<400> SEQUENCE: 5
gctatgctca gatcgccagt                                                 20

<210> SEQ ID NO 6
<211> LENGTH: 22
<212> TYPE: DNA
<213> ORGANISM: Artificial Sequence
<220> FEATURE:
<223> OTHER INFORMATION: Synthetic probe

<400> SEQUENCE: 6
tgctctttgg tggtaatgtg gc                                              22
```